United States Patent
Canning et al.

(10) Patent No.: US 10,441,787 B2
(45) Date of Patent: Oct. 15, 2019

(54) NEUROMODULATION DEVICE

(71) Applicants: GALVANI BIOELECTRONICS LIMITED, Brentford, Middlesex (GB); THE JOHNS HOPKINS UNIVERSITY, Baltimore, MD (US)

(72) Inventors: Brendan J. Canning, Baltimore, MD (US); Michael John Carr, King of Prussia, PA (US); Marian Kollarik, Baltimore, MD (US)

(73) Assignees: GALVANI BIOELECTRONICS LIMITED, Brentford, Middlesex (GB); THE JOHNS HOPKINS UNIVERSITY, Baltimore, MD (US)

(*) Notice: Subject to any disclaimer, the term of this patent is extended or adjusted under 35 U.S.C. 154(b) by 0 days.

(21) Appl. No.: 15/552,475

(22) PCT Filed: Feb. 24, 2016

(86) PCT No.: PCT/US2016/019234
§ 371 (c)(1),
(2) Date: Aug. 21, 2017

(87) PCT Pub. No.: WO2016/138066
PCT Pub. Date: Sep. 1, 2016

(65) Prior Publication Data
US 2018/0043162 A1    Feb. 15, 2018

Related U.S. Application Data

(60) Provisional application No. 62/119,998, filed on Feb. 24, 2015.

(51) Int. Cl.
A61N 1/36  (2006.01)
A61N 1/05  (2006.01)
(Continued)

(52) U.S. Cl.
CPC .......... *A61N 1/36053* (2013.01); *A61F 7/007* (2013.01); *A61N 1/0553* (2013.01);
(Continued)

(58) Field of Classification Search
CPC ............ A61F 2007/0075; A61F 7/007; A61N 2007/0026; A61N 2005/067;
(Continued)

(56) References Cited

U.S. PATENT DOCUMENTS 6,928,320 B2 * 8/2005 King .................. A61N 1/36007
607/46
7,389,145 B2   6/2008 Kilgore et al.
(Continued)

OTHER PUBLICATIONS

International Patent Application No. PCT/US2016/019234; Int'l Written Opinion and Search Report; dated May 23, 2016; 8 pages.
(Continued)

*Primary Examiner* — Catherine M Voorhees
(74) *Attorney, Agent, or Firm* — BakerHostetler

(57) ABSTRACT

The invention provides devices and methods that can prevent or ameliorate bronchoconstriction. In particular, the invention provides devices and methods in which a signal is delivered to the vagus nerve or the pulmonary branches of the vagus nerves. The signal is able to treat bronchoconstriction and prevent and/or ameliorate bronchoconstriction.

1 Claim, 12 Drawing Sheets

Figure 1:
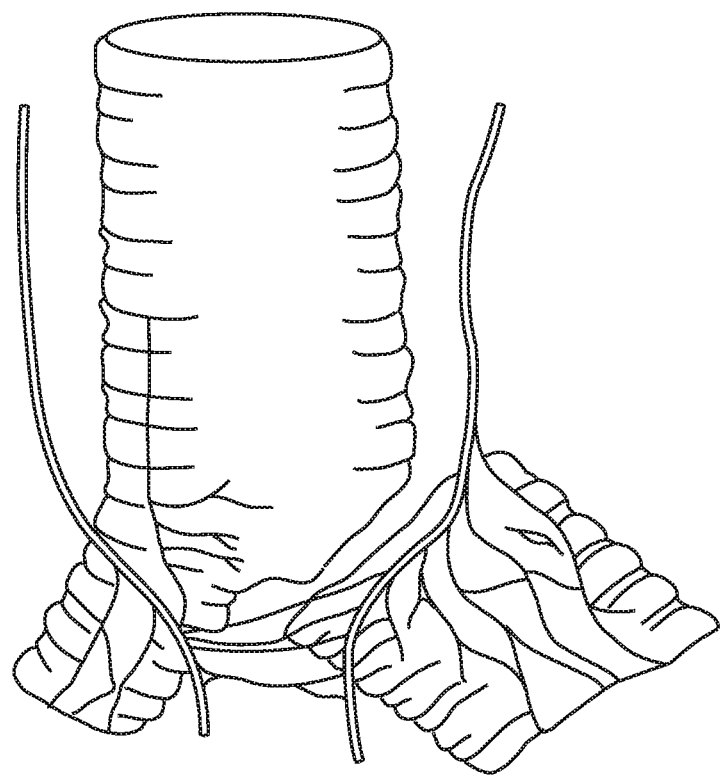

(51) Int. Cl.

| | | |
|---|---|---|
| *A61F 7/00* | (2006.01) | |
| *A61N 1/20* | (2006.01) | |
| *A61N 5/06* | (2006.01) | |
| *A61N 7/00* | (2006.01) | |
| *A61N 5/067* | (2006.01) | |

(52) U.S. Cl.
CPC ........... *A61N 1/205* (2013.01); *A61N 1/3601* (2013.01); *A61N 1/3611* (2013.01); *A61N 1/36014* (2013.01); *A61N 1/36139* (2013.01); *A61N 1/36171* (2013.01); *A61N 1/36178* (2013.01); *A61N 5/0622* (2013.01); *A61N 7/00* (2013.01); *A61F 2007/0075* (2013.01); *A61N 1/36189* (2013.01); *A61N 2005/067* (2013.01); *A61N 2005/0651* (2013.01); *A61N 2007/0026* (2013.01)

(58) Field of Classification Search
CPC ........ A61N 2005/0651; A61N 1/36189; A61N 1/36053; A61N 7/00; A61N 1/205; A61N 1/3611; A61N 5/0622; A61N 1/36014; A61N 1/36178; A61N 1/36171; A61N 1/36139; A61N 1/0553; A61N 1/3601
See application file for complete search history.

(56) References Cited

U.S. PATENT DOCUMENTS

| | | | |
|---|---|---|---|
| 7,747,324 | B2 | 6/2010 | Errico et al. |
| 8,731,676 | B2 | 5/2014 | Fang et al. |
| 2007/0027496 | A1 | 2/2007 | Parnis et al. |
| 2010/0228318 | A1* | 9/2010 | Errico ............... A61N 1/3601 607/42 |
| 2011/0301587 | A1 | 12/2011 | Deem et al. |
| 2013/0238049 | A1 | 9/2013 | Simon et al. |
| 2014/0142653 | A1* | 5/2014 | Osorio ............... A61N 1/36064 607/45 |
| 2014/0186341 | A1 | 7/2014 | Mayse |
| 2014/0222124 | A1* | 8/2014 | Errico ............... A61N 1/36114 607/115 |
| 2014/0257437 | A1* | 9/2014 | Simon ............... A61N 1/0456 607/72 |
| 2014/0371809 | A1 | 12/2014 | Parnis et al. |
| 2015/0202441 | A1* | 7/2015 | Franke ............... A61N 1/3611 606/34 |

OTHER PUBLICATIONS

Hoffman et al.; "Low Voltage Vagal Nerve Stimulation Reduces Bronchoconstriction in Guinea Pigs Through Catecholamine Release"; Neuromodulation; 2012; vol. 15; p. 527-536.

Mazzone et al.; "Guinea Pig Models of Asthma"; Current Protocol Pharmacology; May 2002; Chapter 5 Unit 5.26; 30 pages.

Koopman et al.; "Pilot Study of Stimulation of the Cholinergic Anti-Inflammatory Pathway with an Implantable Vagus Nerve Stimulation Device in Patients with Rheumatoid Arthritis"; Arthritis & Rheumatism; vol. 64 No. 10; Nov. 2012; Abstract No. 451; 2 pages.

Patberg et al.; "Blocking of Impulse Conduction in Peripheral Nerves by Local Cooling as a Routine in Animal Experimentation"; Journal of Neuroscience Methods; 1984; vol. 10; p. 267-275.

Duke et al.; "Spatial and Temporal Variability in Response to Hybrid Electro-Optical Stimulation"; J. Neural Eng.; Jun. 2012; 9(3); 15 pages.

Ritter et al.; "Optogenetic Tools to Suppress Seizures and Explore the Mechanisms of Epileptogenesis"; Epilepsia; Oct. 2014; 55(11); p. 1693-1702.

Kramer et al.; "Optogenetic Pharmacology for Control of Native Neuronal Signaling Proteins"; Nature Neuroscience; Jul. 2013; 16(7); p. 816-823.

Fern et al.; "The Effects of Compression Upon Conduction in Myelinated Axons of the Isolated Frog Sciatic Nerve"; Journal of Physiology; 1991; vol. 432; p. 111-122.

Bhadra et al; "Direct Current Electrical Conduction Block of Peripheral Nerve"; IEEE Transactions on Neural Systems and Rehabilitation Engineering; Sep. 2004; 12(3); p. 313-324.

Kilgore et al.; "Nerve Conduction Block Utilising High-Frequency Alternating Current"; Medical and Biological Engineering and Computing; 2004; vol. 42; p. 394-406.

Bhadra et al.; "Simulation of High-Frequency Sinusoidal Electrical Block of Mammalian Myelinated Axons"; Journal of Computational Neuroscience; 2007; 22(3); p. 313-326.

Canning et al.; "Endogenous Neurokinins Facilitate Synaptic Transmission in Guinea Pig Airway Parasympathetic Ganglia"; Am J. Physiol Regul Integr Comp Physiol.; Aug. 2002; 283(2); p. R320-R330.

Mazzone et al.; "An In Vivo Guinea Pig Preparation for Studying the Autonomic Regulation of Airway Smooth Muscle Tone"; Autonomic Neuroscience; Aug. 2002; 99(2); p. 91-101.

Whitman et al.; "The Use of Direct Current to Cause Selective Block of Large Fibres in Peripheral Nerves"; Br. J. Anaesth.; 1975; vol. 47; p. 1123-1133.

European Patent Application No. 16756233.9; Partial Supplementary Search Report; dated Oct. 18, 2018; 15 pages.

* cited by examiner

BEFORE BLOCK

KILOHERTZ BLOCK
(SINE WAVE, 25kHz, 5V)

AFTER BLOCK

NEUROMODULATION DEVICE

CROSS-REFERENCE TO RELATED APPLICATIONS

This is a national stage application in the United States based on International Application No. PCT/US2016/019234, filed Feb. 24, 2016, which claims priority to U.S. Patent Application No. 62/119,998, filed Feb. 24, 2015, the contents of each of which are incorporated herein by reference in their entirety.

TECHNICAL FIELD

This invention relates to medical devices and, more particularly to medical devices that deliver neuromodulating therapy.

BACKGROUND

Key symptoms in asthma and COPD are the shortness of breath and dyspnea caused by bronchoconstriction, leading to restricted flow of air into the lungs. In conditions such as these, air flow becomes limited as the diameter of the bronchi and bronchioles is reduced in size due to contraction of the airway smooth muscle (ASM) that surrounds those airways. Excessive parasympathetic neural signalling, most likely via cholinergic nerves and corresponding receptors of the ASM, is thought to contribute to such pathological bronchoconstriction.

Small molecule "bronchodilators" reverse contraction of the airway smooth muscle either by acting as agonists for sympathetic neurotransmitter (e.g. catecholamines such as nor-epinephrine and epinephrine) receptors, or by acting as antagonists for the parasympathetic neurotransmitter acetylcholine. For example, beta-adrenoceptor agonists (e.g. salbutamol) act as bronchodilators by activating beta 2 adrenoceptors in airway smooth muscle, which, when activated, cause relaxation of airway smooth muscle. Antimuscarinic bronchodilators (also known as anticholinergics) act by blocking muscarinic receptors in the airway smooth muscle that would otherwise cause bronchoconstriction when activated acetylcholine-mediated parasympathetic signalling.

Modifying the balance between bronchodilatory and bronchoconstrictive signalling has formed the basis for a number of treatments of diseases characterised by bronchoconstriction, such as asthma and COPD. In the early 20$^{th}$ century, denervation—severing the nerves that innervate the lung—was investigated as a therapeutic approach to these diseases. However, such methods were crude and, as the vagus nerve controls numerous organs and body functions besides the lungs and respiration, resulted in significant side-effects. Modern attempts to influence the balance on neural signalling through destructive processes such as partial or whole ablation of the nerves may have similar drawbacks. A further approach has been to stimulate the afferent branches of the vagus nerve to signal the adrenal medulla, thereby causing a release of catecholamines which leads to bronchodilation (Hoffmann et al. Neuromodulation 2012; 15: 527-536, which is incorporated herein by reference in its entirety). However, a systemic increase in circulating catecholamines likely has associated side-effects, such as raised heart rate and raised blood pressure.

Additional methods of alleviating bronchoconstriction would be desirable.

SUMMARY OF INVENTION

The present invention improves over these crude, long-lasting or less-specific interventions for treating bronchoconstriction as a symptom of asthma and/or COPD. The invention provides devices and methods that can prevent or ameliorate bronchoconstriction. These methods or devices may act responsively or on demand, can preserve neuronal structure and function and will be associated with minimal extrapulmonary side-effects. In particular, the invention provides devices and methods in which a signal is delivered to the vagus nerve or the pulmonary branches of the vagus nerves. The signal modulates neural activity in the parasympathetic nerves that normally cause bronchial contraction. The signal is able to treat bronchoconstriction when applied prior to and/or during contraction of the ASM. Thus, such a signal can prevent and/or ameliorate bronchoconstriction.

Therefore, in a first aspect the invention provides an apparatus for modulating the neural activity of the vagus or vagal nerves (these terms may be used interchangeably) of a patient, the apparatus comprising: one or more transducers each configured to apply a signal to a vagal nerve of the patient; and a controller coupled to the one or more transducers, the controller controlling the signal to be applied by each of the one or more transducers, such that the signal modulates the neural activity of the nerve to produce a physiological response in the patient.

In certain embodiments, the signal is an electrical signal. In certain such embodiments, the signal comprises an AC current of kilohertz frequency, optionally of 5-25 kHz, optionally 10-25 kHz, optionally 15-25 kHz, optionally 20-25 kHz. In certain embodiments, the signal at least partially inhibits neural activity in the vagal nerve, optionally fully inhibits neural activity in the nerve. In certain embodiments, the nerve is a pulmonary branch of a vagal nerve, optionally the efferent nerve fibres of a pulmonary branch of a vagal nerve.

In certain embodiments, the physiological response is one or more of: a reduction in parasympathetic tone, a decrease in airway smooth muscle tone, an increase in blood oxygen saturation, a decrease in blood carbon dioxide concentration, a decrease in respiratory rate, an increase in total lung capacity, an increase in forced expiration volume, the action potential or pattern of action potentials in the vagus nerve more closely resembling that exhibited by a healthy individual than before the application of the signal.

In certain embodiments, the apparatus can be used to treat COPD and/or asthma and chronic cough, in particular COPD-associated and asthma associated bronchoconstriction.

In a second aspect the invention provides a method of treating COPD and/or asthma and/or chronic cough, in particular COPD-associated and asthma associated bronchoconstriction, comprising implanting in the patient an apparatus according to the first aspect; positioning at least one transducer of the apparatus in signalling contact with a vagal nerve of the patient; and activating the apparatus. In certain embodiments, a first transducer is positioned in signalling contact with a first vagal nerve (for example, the left vagal nerve) of said patient, and a second transducer is positioned in signalling contact with the contralateral (e.g., the right vagal nerve) of said patient. Alternatively, the first and second transducers can be positioned on the same or ipsilateral vagal nerve. In certain embodiments, the vagal nerve or nerves are each a pulmonary branch (or branches) of a vagal nerve, optionally the efferent fibres of a pulmonary branch (or branches) of a vagal nerve.

In a third aspect the invention provides a method of treating COPD, asthma or chronic cough in a patient, the method comprising applying a signal to a part or all of a vagal nerve of said patient to modulate the neural activity of said nerve in the patient. In certain embodiments the signal is applied to a pulmonary branch of a vagal nerve, optionally the efferent fibres of a pulmonary branch of a vagal nerve. In certain embodiments the signal is applied by a neuromodulation device comprising one or more transducers configured to apply the signal. In certain embodiments, the neuromodulation device is at least partially implanted in the patient, optionally wholly implanted in the patient. In certain embodiments, the modulation in neural activity as a result of applying the signal is at least partial inhibition of neural activity in the nerve to which the signal is applied, optionally full inhibition of neural activity in the nerve to which the signal is applied. In certain embodiments, the signal is an electrical signal. In certain such embodiments, the signal comprises an AC current of kilohertz frequency, optionally of 5-25 kHz, optionally 10-25 kHz, optionally 15-25 kHz, optionally 20-25 kHz.

In a fourth aspect the invention provides a neuromodulatory electrical waveform for use in treating COPD, asthma and chronic cough in a patient, in particular COPD-associated or asthma-associated bronchoconstriction, wherein the waveform is an AC waveform having a frequency of 5-25 kHz, such that, when applied to a vagal nerve, preferably a pulmonary branch of the vagal nerve, of the patient, the waveform inhibits neural signalling in said nerve.

In a fifth aspect the invention provides use of a neuromodulation device for treating COPD, asthma or chronic cough, in particular COPD-associated or asthma-associated bronchoconstriction in a patient by modulating neural activity in a vagal nerve of the patient, preferably a pulmonary branch of the vagal nerve, more preferably the efferent fibres of said pulmonary branch of the vagal nerve.

In a sixth aspect, the invention provides an anti-inflammatory agent, in particular an inhaled anti-inflammatory agent, in particular, an inhaled steroid, for use in a method of treating COPD, asthma or chronic cough, in particular COPD-associated or asthma-associated bronchoconstriction in a patient, wherein the method comprises: applying a signal to a part or all of a vagal nerve of said patient to modulate the neural activity of said nerve in the patient; and administering the anti-inflammatory agent to the patient.

In a preferred embodiment of all aspects of the invention, the patient is a human.

DETAILED DESCRIPTION

Figures

FIG. 1: Schematic showing the vagal nerve innervation of the bronchial tree and a pulmonary branch of the right vagus nerve.

FIG. 2: Schematic drawings showing how apparatuses, devices and methods according to the invention can be put into effect.

Figure 3A:
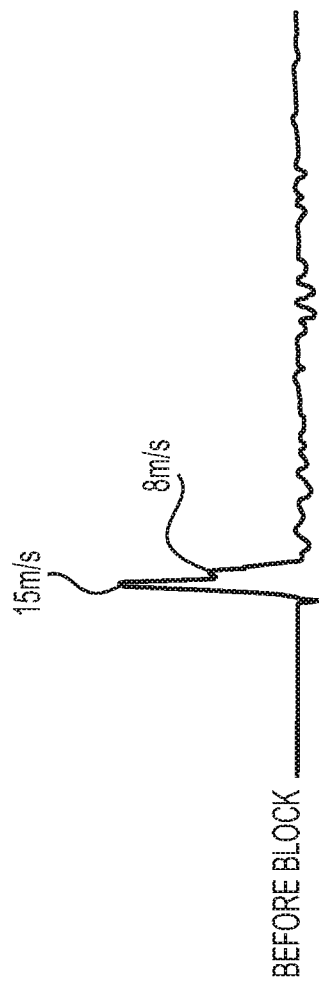

FIG. 3: Block of nerve conduction in the vagus nerve by blocking signal (alternate current 25 kHz, 5V) applied to the vagus nerve. The block was completely reversible.

FIG. 4: Blocking signal (alternate current, AC, 25 kHz, 15V) applied to the vagus nerve (A) completely prevented and (B) nearly completely reversed the nerve activation-induced contraction of airway smooth muscle (bronchoconstriction) ex vivo.

Figure 5A:
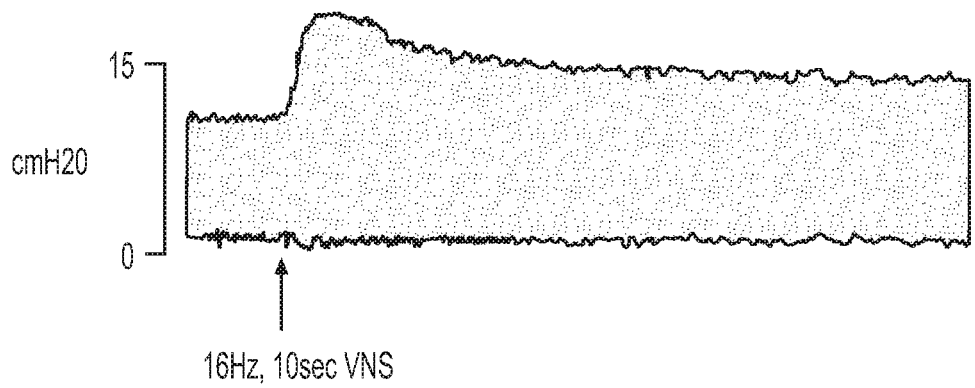
Figure 5B:
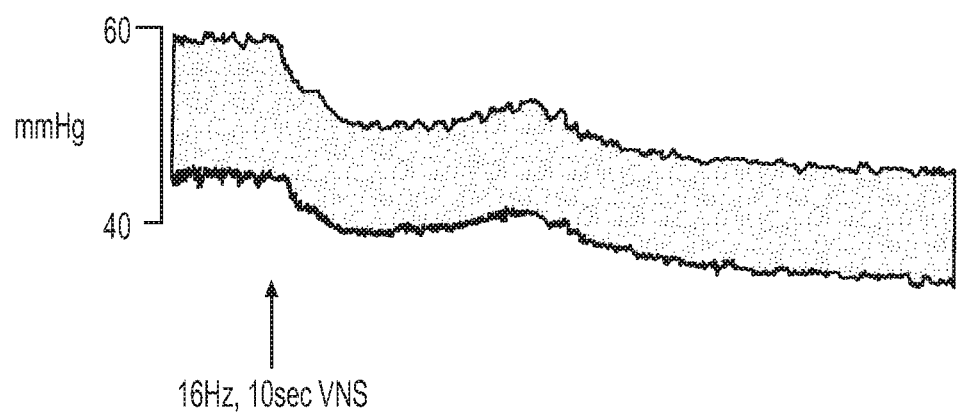

FIG. 5: Vagally-induced bronchospasm (measured as an increase in pulmonary inflation pressure) in vivo.

Figure 6:
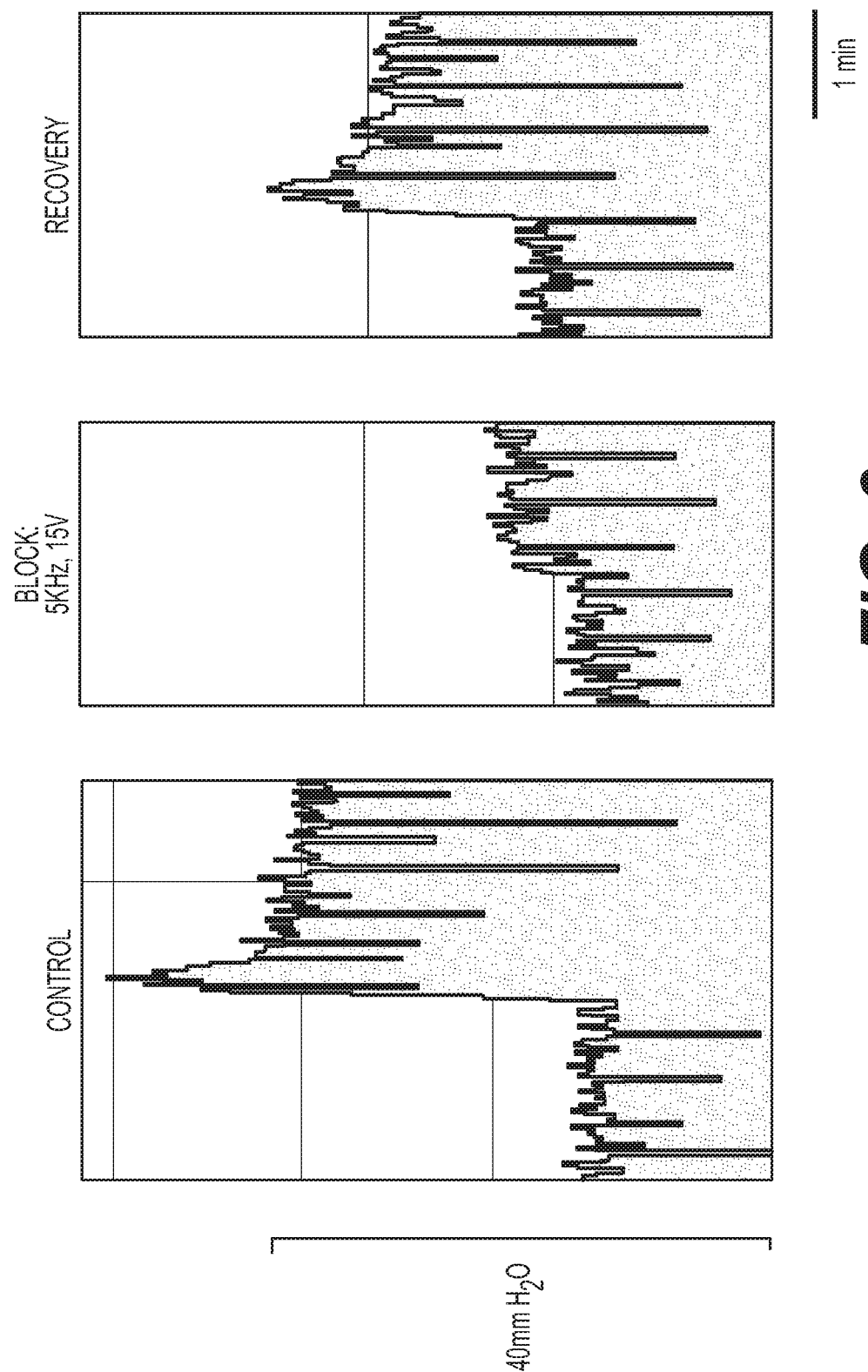

FIG. 6: Block of vagally-mediated bronchospasm in vivo by blocking signal (alternate current, 5 KHz, 5V) applied to the vagus nerve.

Figure 7:

FIG. 7: Block of pulmonary nerve fibers in the pulmonary branch of the vagus nerve by blocking signal (alternate current, 5 kHz, 3V) applied to the pulmonary branch of the vagus nerve. The block was completely reversible.

Figure 8:
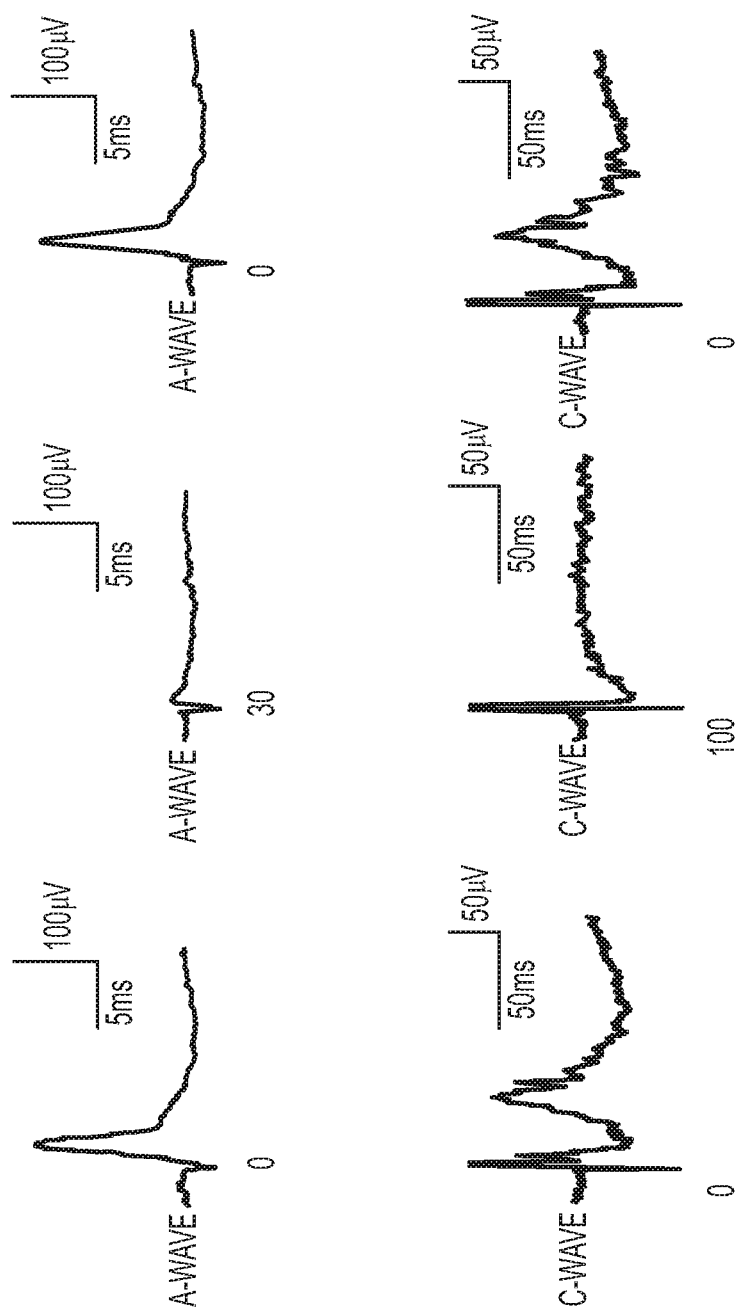

FIG. 8: Inhibition of compound action potential amplitude in Guinea Pig vagus ex-vivo by application of Direct Current (DC) blocking signal. A-wave (upper panel) and C wave (lower panel) compound action potentials (µA) were recorded prior to application (left), during application (center) and after the blocking signal had been turned off (right).

Figure 9:
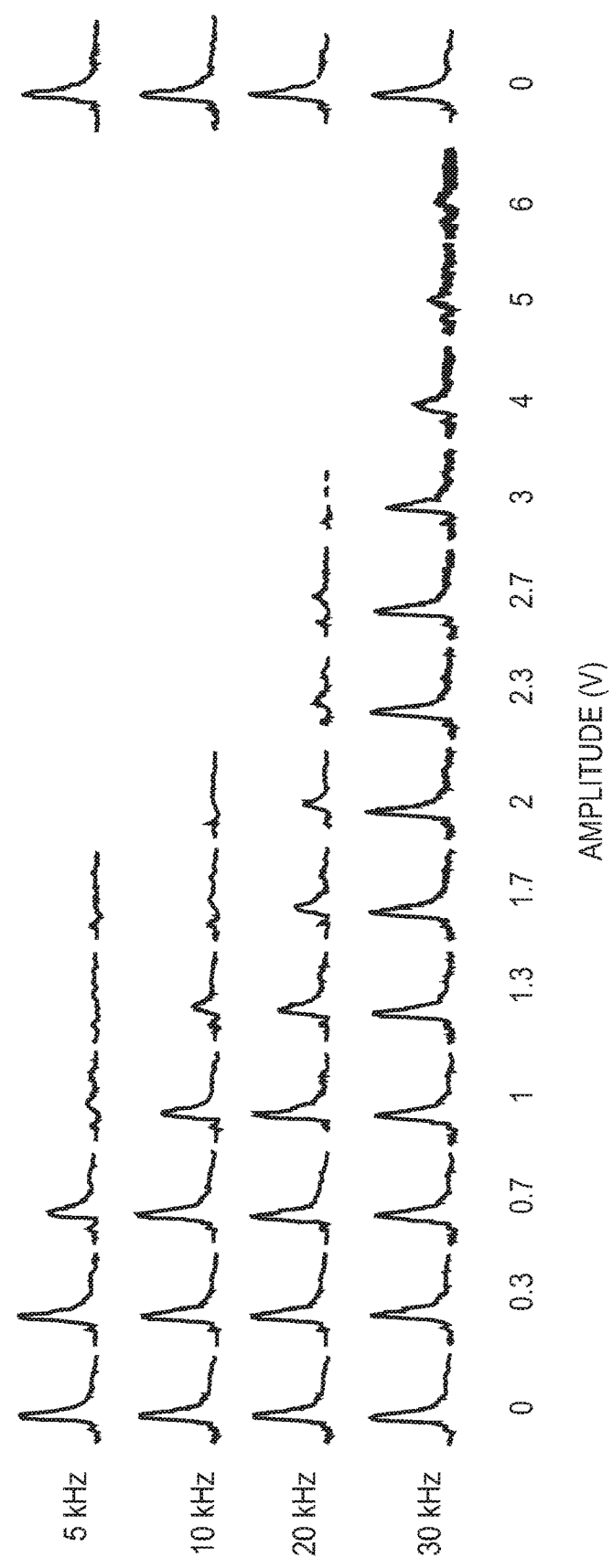

FIG. 9: Inhibition of compound action potential amplitude in a human thoracic vagus brach ex-vivo by application of a Kilohertz Frequency blocking signal.

Figure 10:
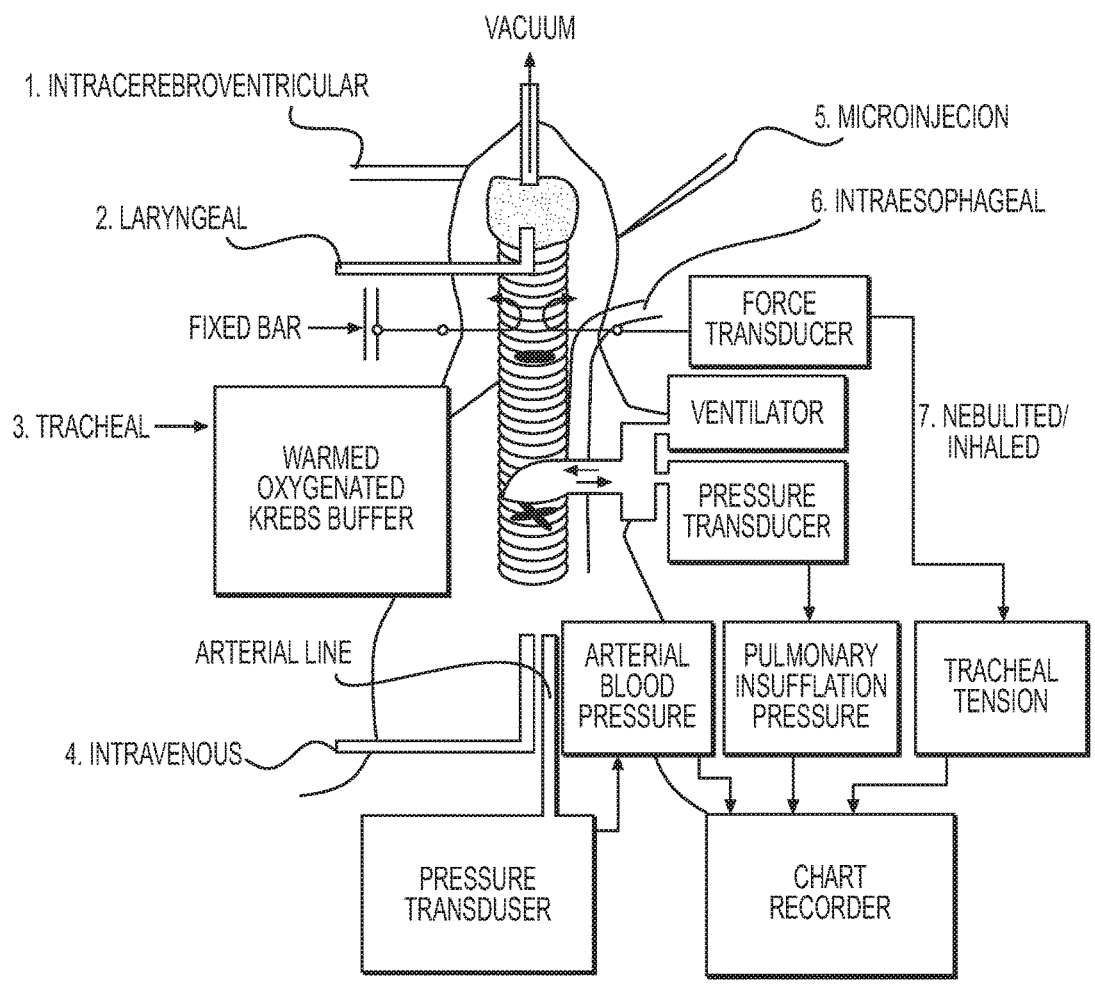

FIG. 10: Schematic illustration of the method for assessing vagally-mediated baseline airay smooth muscle tone in anesthetized guinea pigs. (As described in, Mazzone and Canning, Curr. Protoc. Pharmacol. 2002. May 1; Chapter 5: Unit 5.26.)

Figure 11:
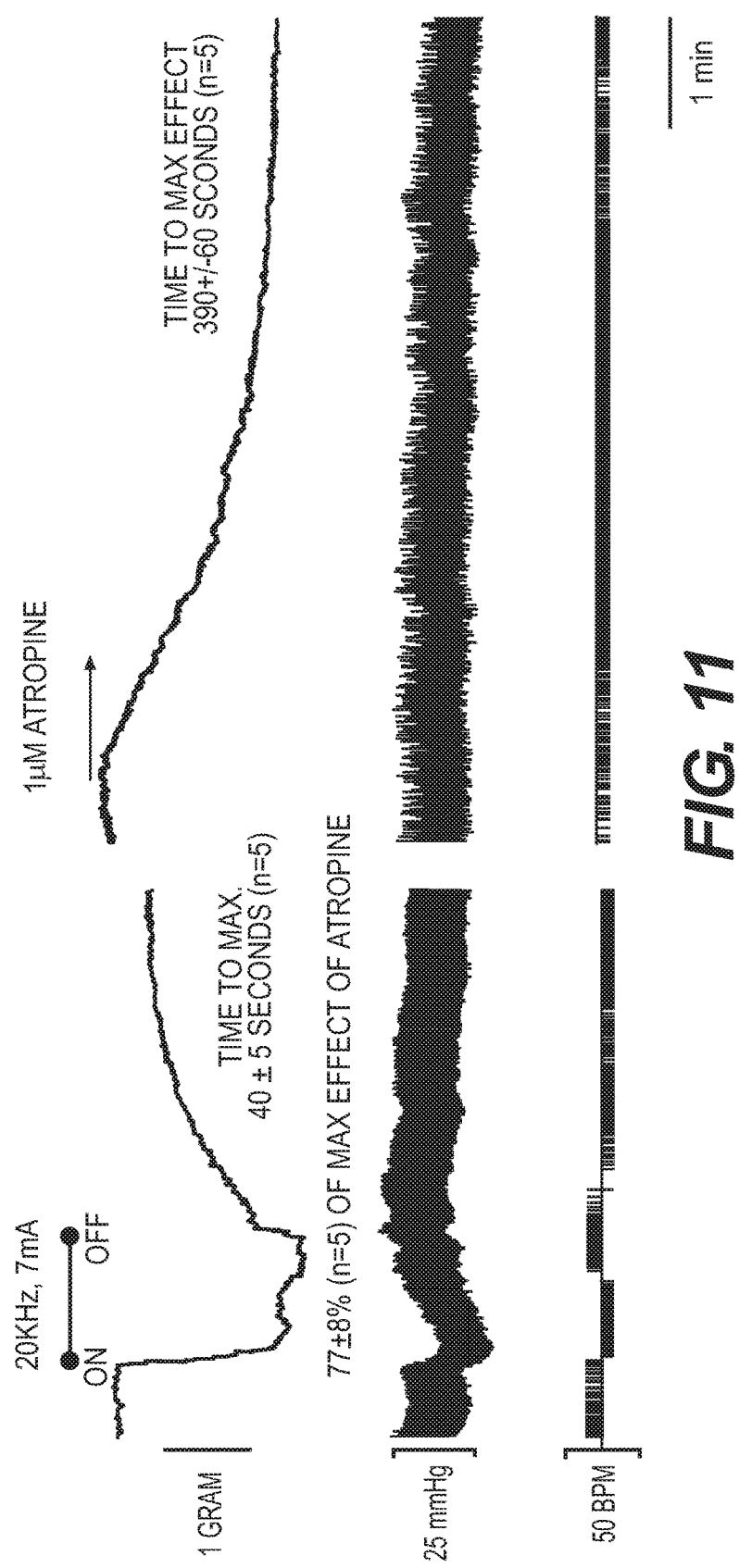

FIG. 11: Inhibition of guinea pig airway smooth muscle tone in vivo by application of a blocking signal to the left and right vagus nerves or application of atropine directly to the airway smooth muscle. The upper trace is a record of airway smooth muscle tone. The middle trace is a record of blood pressure and the lower trace is a record of heart rate.

Figure 12:
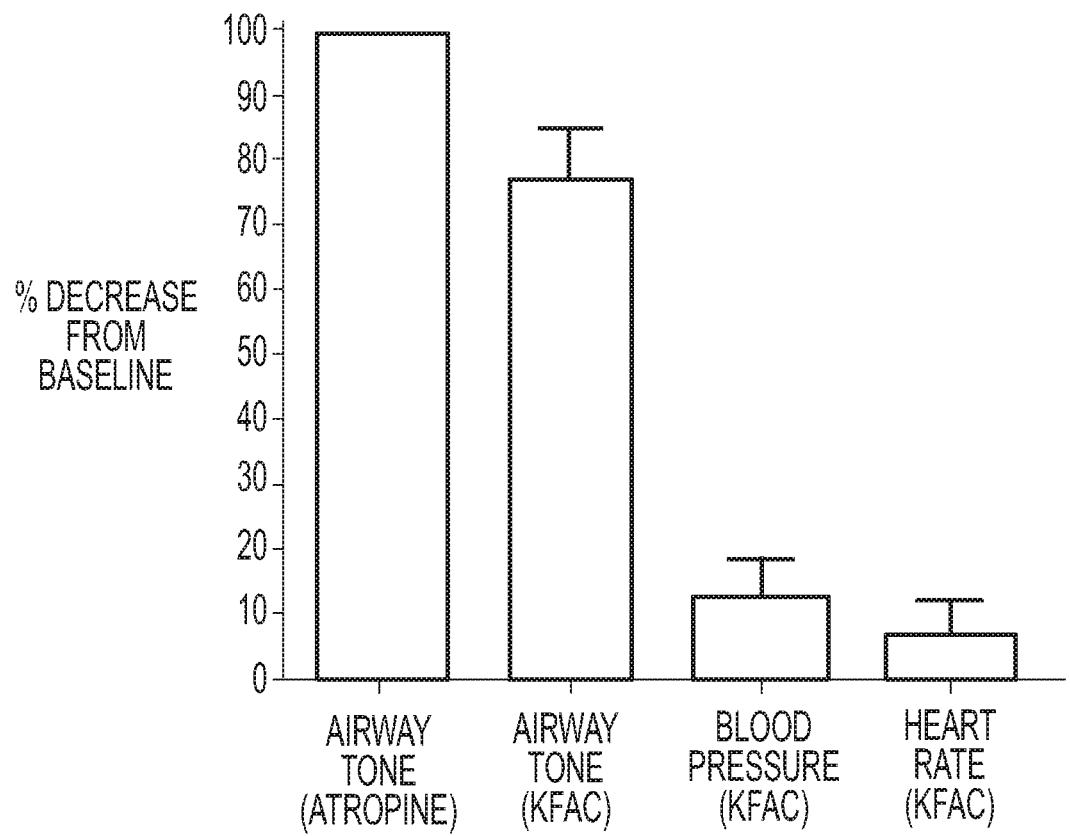

FIG. 12: Influence of a nueromodulatory signal (KFAC, Alternating Current, 20 kHz, 5-7 mA, n=5) applied to the left and right vagus nerves on baseline airway tone, heart rate and blood pressure in anesthetized guinea pigs (n=4-5).

The terms as used herein are given their conventional definition in the art as understood by the skilled person, unless otherwise defined below. In the case of any inconsistency or doubt, the definition as provided herein should take precedence.

As used herein, application of a signal may equate to the transfer of energy in a suitable form to carry out the intended effect of the signal. That is, application of a signal to a nerve or nerves may equate to the transfer of energy to (or from) the nerve(s) to carry out the intended effect. For example, the energy transferred may be electrical, mechanical (including acoustic, such as ultrasound), electromagnetic (e.g. optical), magnetic or thermal energy. It is noted that application of a signal as used herein does not include a pharmaceutical intervention.

As used herein, a "non-destructive signal" is a signal as defined above that, when applied, does not irreversibly damage the underlying neural signal conduction ability. That is, application of a non-destructive signal maintains the ability of the nerve or nerves (or fibres thereof) to conduct action potentials when application of the signal ceases, even if that conduction is in practice inhibited or blocked as a result of application of the non-destructive signal. Ablation and cauterisation of at least part of the nerve are examples of destructive signals.

As used herein, "neural activity" of a nerve is taken to mean the signalling activity of the nerve, for example the amplitude, frequency and/or pattern of action potentials in the nerve.

Modulation of neural activity, as used herein, is taken to mean that the signalling activity of the nerve is altered from the baseline neural activity—that is, the signalling activity of the nerve in the patient prior to any intervention. Such modulation may increase, inhibit (for example block), or otherwise change the neural activity compared to baseline activity.

Where the modulation of neural activity is an increase of neural activity, this may be an increase in the total signalling activity of the whole nerve, or that the total signalling activity of a subset of nerve fibres of the nerve is increased, compared to baseline neural activity in that part of the nerve.

Where the modulation of neural activity is inhibition of neural activity, such inhibition may be partial inhibition. Partial inhibition may be such that the total signalling activity of the whole nerve is partially reduced, or that the total signalling activity of a subset of nerve fibres of the nerve is fully reduced (i.e. there is no neural activity in that subset of fibres of the nerve), or that the total signalling of a subset of nerve fibres of the nerve is partially reduced compared to neural activity in that subset of fibres of the nerve prior to intervention. Where the modulation of neural activity is inhibition of neural activity, this also encompasses full inhibition of neural activity in the nerve.

Inhibition of neural activity may be a block on neural activity. Such blocking may be a partial block—i.e. blocking of neural activity in a subset of nerve fibres of the nerve. Alternatively, such blocking may be a full block—i.e. blocking of neural activity across the whole nerve. A block on neural activity is understood to be blocking neural activity from continuing past the point of the block. That is, when the block is applied, action potentials may travel along the nerve or subset of nerve fibres to the point of the block, but not beyond the block.

Modulation of neural activity may also be an alteration in the pattern of action potentials. It will be appreciated that the pattern of action potentials can be modulated without necessarily changing the overall frequency or amplitude. For example, modulation of the neural activity may be such that the pattern of action potentials is altered to more closely resemble a healthy state rather than a disease state.

Modulation of neural activity may comprise altering the neural activity in various other ways, for example increasing or inhibiting a particular part of the neural activity and/or stimulating new elements of activity, for example in particular intervals of time, in particular frequency bands, according to particular patterns and so forth. Such altering of neural activity may for example represent both increases and/or decreases with respect to the baseline activity.

Modulation of the neural activity may be temporary. As used herein, "temporary" is taken to mean that the modulated neural activity (whether that is an increase, inhibition, block or other modulation of neural activity or change in pattern versus baseline activity) is not permanent. That is, the neural activity following cessation of the signal is substantially the same as the neural activity prior to the signal being applied—i.e. prior to modulation.

Modulation of the neural activity may be persistent. As used herein, "persistent" is taken to mean that the modulated neural activity (whether that is an increase, inhibition, block or other modulation of neural activity or change in pattern versus baseline activity) has a prolonged effect. That is, upon cessation of the signal, neural activity in the nerve remains substantially the same as when the signal was being applied—i.e. the neural activity during and following modulation is substantially the same.

Modulation of the neural activity may be corrective. As used herein, "corrective" is taken to mean that the modulated neural activity (whether that is an increase, inhibition, block or other modulation of neural activity or change in pattern versus baseline activity) alters the neural activity towards the pattern of neural activity in a healthy individual. That is, upon cessation of the signal, neural activity in the nerve more closely resembles the pattern of action potentials in the nerve observed in a healthy subject than prior to modulation, preferably substantially fully resembles the pattern of action potentials in the nerve observed in a healthy subject.

Such corrective modulation caused by the signal can be any modulation as defined herein. For example, application of the signal may result in a block on neural activity, and upon cessation of the signal, the pattern of action potentials in the nerve resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy individual.

As used herein, bronchoconstriction and bronchospasm are used interchangeably to mean aberrant contraction of the airway smooth muscle (ASM). The skilled person will appreciate that in a healthy individual there is an ongoing background level of ASM contraction. Aberrant contraction of the ASM is a level of contraction that exceeds this background level. Bronchoconstriction may be acute or chronic, transient or permanent. An aberrant contraction of the airway smooth muscle (ASM) may be characterised by, for example, shortness of breath or wheezing. Causes of aberrant contractions of the airway smooth muscle (ASM) include (but are not limited to) pulmonary inflammation, pulmonary infection, stress, sensory irritation and allergens. Bronchoconstriction is one of the symptoms of both chronic obstructive pulmonary disease (COPD) and asthma.

As used herein, the neural activity in the vagus nerve of a healthy individual is that neural activity exhibited by a patient not undergoing bronchoconstriction.

As used herein, an "improvement in a measurable physiological parameter" is taken to mean that for any given physiological parameter, an improvement is a change in the value of that parameter in the patient towards the normal value or normal range for that value—i.e. towards the expected value in a healthy individual.

For an example, in a patient suffering from asthma or COPD, an improvement in a measurable parameter may be: a reduction in parasympathetic tone, a decrease in airway smooth muscle tone, an increase in blood oxygen saturation, a decrease in blood carbon dioxide concentration, a decrease in respiratory rate, an increase in total lung capacity, an increase in forced expiration volume.

The physiological parameter may comprise an action potential or pattern of action potentials in a nerve of the patient. An improvement in such a parameter is characterised by the action potential or pattern of action potentials in the nerve more closely resembling that exhibited by a healthy individual than before the intervention.

As used herein, a physiological parameter is not affected by modulation of the neural activity if the parameter does not change as a result of the modulation from the average value of that parameter exhibited by the subject or patient when no intervention has been performed—i.e. it does not depart from the baseline value for that parameter.

The skilled person will appreciate that the baseline for any neural activity or physiological parameter in an individual need not be a fixed or specific value, but rather can fluctuate within a normal range or may be an average value with associated error and confidence intervals. Suitable methods for determining baseline values would be well known to the skilled person.

As used herein, a measurable physiological parameter is detected in a patient when the value for that parameter exhibited by the patient at the time of detection is determined. A detector is any element able to make such a determination.

A "predefined threshold value" for a physiological parameter is the value for that parameter where that value or beyond must be exhibited by a subject or patient before the intervention is applied. For any given parameter, the threshold value may be a value indicative of imminent or ongoing bronchospasm. Examples of such predefined threshold values include parasympathetic tone (neural, hemodynamic (e.g. heart rate, blood pressure, heart rate variability) or circulating plasma/urine biomarkers) greater than a threshold parasympathetic tone, or greater than parasympathetic tone in a healthy individual; ASM tone greater than a threshold ASM tone, or greater than ASM tone in a healthy individual; blood oxygen saturation lower than that characteristic of a healthy individual; blood carbon dioxide concentration greater than that characteristic of a healthy individual; a total lung capacity lower than that characteristic of a healthy individual; a forced expiration volume lower than that characteristic of a healthy individual. Appropriate values for any given parameter would be simply determined by the skilled person.

Such a threshold value for a given physiological parameter is exceeded if the value exhibited by the patient is beyond the threshold value—that is, the exhibited value is a greater departure from the normal or healthy value for that parameter than the predefined threshold value.

Treatment of COPD and treatment of asthma as used herein is characterised at least by treatment of bronchoconstriction associated with said conditions. Treatment may be prophylactic or therapeutic. Prophylactic treatment may be characterised by the patient exhibiting less frequent or less severe episodes of bronchoconstriction than before treatment. Therapeutic treatment may be characterised by amelioration of an ongoing bronchospasm. For example, therapeutic treatment is applied when the patient is experiencing bronchoconstriction and results in at least partial relief of the bronchoconstriction, preferably full relief of the bronchoconstriction (i.e. a return to healthy levels).

A "neuromodulation device" as used herein is a device configured to modulate the neural activity of a nerve. Neuromodulation devices as described herein comprise at least one transducer capable of effectively applying a signal to a nerve. In those embodiments in which the neuromodulation device is at least partially implanted in the patient, the elements of the device that are to be implanted in the patient are constructed such that they are suitable for such implantation. Such suitable constructions would be well known to the skilled person. Indeed, various fully implantable neuromodulation devices are currently available, such as the vagus nerve stimulator of SetPoint Medical, in clinical development for the treatment of rheumatoid arthritis (*Arthritis & Rheumatism*, Volume 64, No. 10 (Supplement), page S195 (Abstract No. 451), October 2012. *"Pilot Study of Stimulation of the Cholinergic Anti-Inflammatory Pathway with an Implantable Vagus Nerve Stimulation Device in Patients with Rheumatoid Arthritis"*, Frieda A. Koopman et al), and the INTERSTIM™ device (Medtronic, Inc), a fully implantable device utilised for sacral nerve modulation in the treatment of overactive bladder.

As used herein, "implanted" is taken to mean positioned at least partially within the patient's body. Partial implantation means that only part of the device is implanted—i.e. only part of the device is positioned within the patient's body, with other elements of the device external to the patient's body. Wholly implanted means that the entire of the device is positioned within the patient's body.

As used herein, "charge-balanced" in relation to a DC current is taken to mean that the positive or negative charge introduced into any system (e.g. a nerve) as a result of a DC current being applied is balanced by the introduction of the opposite charge in order to achieve overall (i.e. net) neutrality.

As shown herein, it has been identified that bronchoconstriction, such as COPD-associated and asthma-associated bronchoconstriction can be relieved and/or prevented by modulation of the neural activity of a vagus nerve—that is, a nerve or nerve fibres ultimately derived from the tenth cranial nerve (CN X) and branches thereof. Surprisingly, it is particularly advantageous to modulate the neural activity of a pulmonary branch of the vagal nerve to treat said bronchoconstriction. Doing so limits the possibility of unwanted side-effects on other bodily systems controlled by the vagus nerve. It is further identified herein that, surprisingly, it is advantageous to modulate the effector fibres of a pulmonary branch of the vagal nerve, as these are the nerve fibres acting directly on the airway smooth muscle (ASM). By targeting these nerves fibres, it is therefore intended to further limit side-effects and cross-reactivity associated with the neuromodulation.

A neuromodulation device that modulates the parasympathetic neural activity in a vagal nerve will therefore provide an effective treatment for COPD and for asthma.

Such a device can be advantageously used in conjunction with pharmacological approaches for the treatment of bronchoconstriction, COPD, and chronic cough. In particular, such a device would permit better delivery of therapeutic agents by inhalation. In an embodiment, the therapeutic agent delivered by inhalation may be an inhalable anti-inflammatory agent, optionally a steroid, such as beclomethasone proprionate, budesonide, ciclesonide, flunisolide, fluticasone proprionate, mometasone, triamcinolone acetonide. Alternatively, such a device can be employed in conjunction with administration of a steroidal or non-steroidal anti-inflammatory agent, a therapeutic antibody with anti-inflammatory effects and/or a cytokine with anti-inflammatory effects. In each case such administration can be by conventional means.

Therefore, in accordance with a first aspect of the invention there is provided an apparatus for modulating the neural activity of a vagal nerve of a patient, the apparatus comprising: one or more transducers configured to apply a signal to the nerve, optionally at least two such transducers; and a controller coupled to the transducer or transducers, the controller controlling the signal to be applied by the one or more transducers, such that the signal modulates the neural activity of the nerve to produce a physiological response in the patient.

In certain embodiments, the signal applied by the one or more transducers is a non-destructive signal.

In certain such embodiments, the signal applied by the one or more transducers is an electrical signal, an optical signal, an ultrasonic signal, or a thermal signal. In those embodiments in which the apparatus has at least two transducers, the signal which each of the transducers is configured to apply is independently selected from an electrical signal, an optical signal, an ultrasonic signal, and a thermal signal. That is, each transducer may be configured to apply a different signal. Alternatively, in certain embodiments each transducer is configured to apply the same signal.

In certain embodiments, each of the one or more transducers may be comprised of one or more electrodes, one or more photon sources, one or more ultrasound transducers, one more sources of heat, or one or more other types of transducer arranged to put the signal into effect.

In certain embodiments, the signal or signals applied by the one or more transducers is an electrical signal, for example a voltage or current. In certain such embodiments the signal applied comprises a direct current (DC) waveform, such as a charge balanced direct current waveform, or an alternating current (AC) waveform, or both a DC and an AC waveform. In certain embodiments, the signal comprises an AC waveform of kilohertz frequency.

In certain embodiments the signal comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform. In certain such embodiments, the DC ramp, first AC waveform and second AC waveform are applied substantially sequentially.

In certain preferred embodiments, wherein the signal comprises one or more AC waveforms, each AC waveform is independently selected from an AC waveform of 5-25 kHz, optionally 10-25 kHz, optionally 15-25 kHz, optionally 20-25 kHz. In certain preferred embodiments, the signal comprises an AC waveform signal of 5 kHz. In certain alternative preferred embodiments, the signal comprises an AC waveform of 25 kHz.

In certain embodiments, the signal comprises a DC waveform and/or an AC waveform having a voltage of 1-20V. In certain preferred embodiments, the signal has a voltage of 1-15V, 3-15V, 5-15V, optionally 10-15V. In certain preferred embodiments the voltage is selected from 3V, 5V, 10V and 15V.

In certain preferred embodiments, the signal comprises an AC waveform of 5 kHz 3V, or an AC waveform of 5 kHz 15V, or an AC waveform of 25 kHz 5V, or an AC waveform of 25 kHz 10V.

It has previously been thought in the field that high frequency AC signals applied to nerves are disadvantageous, as the high frequencies were thought to result in an unwanted DC effect that could damage the nerves, disrupting their ability to carry action potentials. It is identified herein that, surprisingly, the indicated high frequency electrical signals are able to effectively modulate the neural activity of the nerve without damaging the nerve (as shown by the recovery of the neural activity following cessation of the signal (see Examples)).

In those embodiments in which the signal applied by the one or more transducers is an electrical signal, at least one of the one or more transducers is an electrode configured to apply the electrical signal. In certain such embodiments, all the transducers are electrodes configured to apply an electrical signal, optionally the same electrical signal.

In certain embodiments wherein the signal applied by the one or more transducers is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In those embodiments in which the signal applied by the one or more transducers is a thermal signal, at least one of the one or more transducers is a transducer configured to apply a thermal signal. In certain such embodiments, all the transducers are configured to apply a thermal signal, optionally the same thermal signal.

In certain embodiments, one or more of the one or more transducers comprise a Peltier element configured to apply a thermal signal, optionally all of the one or more transducers comprise a Peltier element. In certain embodiments, one or more of the one or more transducers comprise a laser diode configured to apply a thermal signal, optionally all of the one or more transducers comprise a laser diode configured to apply a thermal signal. In certain embodiments, one or more of the one or more transducers comprise a electrically resistive element configured to apply a thermal signal, optionally all of the one or more transducers comprise a electrically resistive element configured to apply a thermal signal.

In certain embodiments the signal applied by the one or more transducers is a mechanical signal, optionally an ultrasonic signal. In certain alternative embodiments, the mechanical signal applied by the one or more transducers is a pressure signal.

In certain embodiments the signal applied by the one or more transducers is an electromagnetic signal, optionally an optical signal. In certain such embodiments, the one or more transducers comprise a laser and/or a light emitting diode configured to apply the optical signal.

In certain embodiments, the physiological response produced in the patient is one or more of: a reduction in parasympathetic tone, a decrease in airway smooth muscle tone, an increase in blood oxygen saturation, a decrease in blood carbon dioxide concentration, a decrease in respiratory rate, an increase in total lung capacity, an increase in forced expiration volume, an increase in peak expiratory flow, reduced dyspnea, reduced cough, and the pattern of action potentials in the vagus nerve more closely resembling that exhibited by a healthy individual than before the intervention.

In certain embodiments, the apparatus further comprises a detector element to detect one or more physiological parameters in the patient. Such a detector element may be configured to detect the one or more physiological parameters. That is, in such embodiments each detector may detect more than one physiological parameter, for example all the detected physiological parameters. Alternatively, in such embodiments each of the one or more detector elements is configured to detect a separate parameter of the one or more physiological parameters detected.

In such certain embodiments, the controller is coupled to the detector element configured to detect one or more physiological parameters, and causes the transducer or transducers to apply the signal when the physiological parameter is detected to be meeting or exceeding a predefined threshold value.

In certain embodiments, the one or more detected physiological parameters are selected from: parasympathetic tone, ASM tone, blood oxygen saturation, blood carbon dioxide concentration, respiratory rate, total lung capacity, and forced expiration volume.

In certain embodiments, the one or more detected physiological parameters comprise an action potential or pattern of action potentials in a nerve of the patient, wherein the action potential or pattern of action potentials is associated with bronchoconstriction. In certain such embodiments, the nerve is a vagal nerve. In certain such embodiments, the nerve is a pulmonary branch of the vagal nerve. In certain embodiments, the action potential or pattern of action potentials is detected in efferent fibres of a vagal nerve, preferably efferent fibres of a pulmonary branch of the vagal nerve. Alternatively, in certain embodiments, the action potential or pattern of action potentials is detected in afferent fibres of a vagal nerve, preferably afferent fibres of a pulmonary branch of the vagal nerve.

It will be appreciated that any two or more of the indicated physiological parameters may be detected in parallel or consecutively. For example, in certain embodiments, the controller is coupled to a detector or detectors configured to detect the pattern of action potentials in a pulmonary branch of a vagal nerve and also the blood oxygen saturation of the patient.

The inventors have identified that bronchoconstriction can be relieved and/or prevented by modulation of the neural activity of a vagus nerve—that is, by modulating the neural activity in a nerve ultimately derived from the tenth cranial nerve (CN X) and branches thereof. Surprisingly, it is particularly advantageous to modulate the neural activity of a pulmonary branch of the vagal nerve to treat bronchoconstriction associated with COPD or asthma. Doing so will limit the possibility of unwanted side-effects on other bodily systems controlled by the vagus nerve. It will be further advantageous to modulate the effector fibres of a pulmonary branch of the vagal nerve, as these are the nerve fibres acting directly on the ASM. By targeting these nerves fibres, it is therefore intended to further limit side-effects and cross-reactivity associated with the neuromodulation.

Therefore, in certain embodiments, the signal is applied is to a pulmonary branch of the vagal nerve. In certain preferred embodiments, the signal is applied to the efferent fibres of a pulmonary branch of the vagal nerve. In certain embodiments, the signal is applied to the specified nerve on the left-side of the patient, the specified nerve on the right-side of the patient, or both. Optional signals can be applied to more than one point on the same side of the patient.

In certain embodiments, the modulation in neural activity as a result of applying the signal is an increase in neural activity in the nerve or nerves to which the signal is applied. That is, in such embodiments, application of the signal results in the neural activity in at least part of the nerve or nerves being increased compared to the baseline neural activity in that part of the nerve. Such an increase in activity could equally be across the whole nerve, in which case neural activity would be increased across the whole nerve or nerves. Therefore, in certain such embodiments, a result of applying the signal is an increase in neural activity in the nerve or nerves. In certain embodiments, a result of applying the signal is an increase in neural activity across the whole nerve or nerves.

In certain embodiments, the modulation in neural activity as a result of applying the signal is an alteration to the pattern of action potentials in the nerve or nerves. In certain such embodiments, the neural activity is modulated such that the resultant pattern of action potentials in the nerve or nerves resembles the pattern of action potentials in the nerve or nerves observed in a healthy subject.

It is further identified herein that, surprisingly, inhibiting the neural activity in a vagal nerve of the patient is especially effective at treating bronchoconstriction, as applying an inhibitory signal restores pulmonary inflation pressure (FIG. 6).

Therefore, in certain embodiments the modulation in neural activity as a result of applying the signal is inhibition of neural activity in the part of the nerve or nerves to which the signal is applied. That is, in such embodiments, application of the signal results in the neural activity being reduced compared to the neural activity in that part of the nerve prior to the signal being applied.

In certain embodiments, the inhibition in neural activity as a result of applying the signal is a block on neural activity in the part of the nerve or nerves to which the signal is applied. That is, in such embodiments, the application of the signal blocks action potentials from travelling beyond the point of the block. In certain such embodiments, the modulation is a partial block—that is, neural activity is blocked in part of the nerve to which the signal is applied, for example a subset of nerve fibres. In certain alternative embodiments, the modulation is a full block—that is, neural activity is blocked in all of the nerve to which the signal is applied.

The inventors have identified that application certain signals (for example, some high frequency AC signals) can, in some cases, result in an initial stimulation of the nerve—so-called onset effect. This onset effect may be unwanted in some instances where the signal is intended to inhibit neural activity.

Therefore, in certain embodiments the signal applied to the nerve is a signal that inhibits (e.g. blocks) neural activity and limits or prevents onset effect.

An example of such a signal that limits or prevents onset effect is a signal that comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform, as described above.

In certain preferred embodiments, the signal applied to the nerve is an electrical signal comprising an AC waveform of kilohertz frequency such that the neural activity in the nerve is inhibited, preferably blocked. In certain preferred such embodiments, the nerve is a pulmonary branch of the vagal nerve, preferably the efferent fibres of a pulmonary branch of the vagal nerve. In certain preferred embodiments, the signal comprises an AC waveform of 5 kHz 3V, optionally an AC waveform of 5 kHz 15V, optionally an AC waveform of 25 kHz 5V, optionally an AC waveform of 25 kHz 5V.

Modulation of neural activity may comprise altering the neural activity in various other ways, for example increasing or inhibiting a particular part of the activity and stimulating new elements of activity, for example in particular intervals of time, in particular frequency bands, according to particular patterns and so forth. Such altering of neural activity may for example represent both increases and/or decreases with respect to the baseline activity.

In certain embodiments, the controller causes the signal to be applied intermittently. In certain such embodiments, the controller causes the signal to applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the controller causes the signal to be applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the controller causes the signal to be applied intermittently, the signal is applied only when the patient is in a specific physiological state. In certain such embodiments, the signal is applied only when the patient is in a state of bronchospasm.

In certain such embodiments, the apparatus further comprises a communication, or input, element via which the status of the patient (e.g. that they are experiencing bronchospasm) can be indicated by the patient or a physician. In alternative embodiments, the apparatus further comprises a detector configured to detect the status of the patient, wherein the signal is applied only when the detector detects that the patient is in the specific state.

In certain alternative embodiments, the controller causes the signal to be permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the apparatus, the modulation in neural activity caused by the application of the signal (whether that is an increase, inhibition, block or other modulation of neural activity) is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the modulation in neural activity caused by the application of the signal or signals is substantially persistent. That is, upon cessation of the signal, neural activity in the nerve or nerves remains substantially the same as when the signal was being applied—i.e. the neural activity during and following modulation is substantially the same.

In certain embodiments, the modulation in neural activity caused by the application of the signal is partially corrective, preferably substantially corrective. That is, upon cessation of the signal, neural activity in the nerve or nerves more closely resembles the pattern of action potentials in the nerve(s) observed in a healthy subject than prior to modulation, preferably substantially fully resembles the pattern of action potentials in the nerve(s) observed in a healthy subject. In such embodiments, the modulation caused by the signal can be any modulation as defined herein. For example, application of the signal may result in a block on neural activity, and upon cessation of the signal, the pattern of action potentials in the nerve or nerves resembles the pattern of action potentials observed in a healthy individual. By way of further example, application of the signal may result in modulation such that the neural activity resembles the pattern of action potentials observed in a healthy subject, and upon cessation of the signal, the pattern of action potentials in the nerve or nerves resembles the pattern of action potentials observed in a healthy subject. It is hypothesised that such a corrective effect is the result of a positive feedback loop—that is, the underlying predisposition to bronchoconstriction caused by asthma or COPD is treated as result of the device and use in the claimed methods.

In certain embodiments, the apparatus is suitable for at least partial implantation into the patient. In certain such embodiments, the apparatus is suitable to be fully implanted in the patient.

In certain embodiments, the apparatus further comprises one or more power supply elements, for example a battery, and/or one or more communication elements.

In a second aspect, the invention provides a method for treating COPD or asthma in a patient, in particular bronchoconstriction associated with COPD or asthma, the method comprising implanting an apparatus according to the first aspect, positioning at least one transducer of the apparatus in signalling contact with a vagal nerve of the patient, and activating the apparatus. In such embodiments, the transducer is in signalling contact with the nerve when it is positioned such that the signal can be effectively applied to the nerve. The apparatus is activated when the apparatus is in an operating state such that the signal will be applied as determined by the controller.

In certain such embodiments, a first transducer is positioned in signalling contact with a first (e.g., left) vagal nerve of said patient to modulate the neural activity of said first (e.g., left) nerve in the patient, and a second transducer is positioned in signalling contact with a contralateral (e.g., right) vagal nerve of said patient to modulate the neural activity of said contralateral (e.g., right) nerve in the patient. Alternatively, a first and second transducer can be positioned in signalling contact with different sites on the same (ipsilateral) vagal nerve. In certain such embodiments, the first and second transducers are part of one apparatus according to the first aspect. In alternative such embodiments, the first and second transducers are part of separate apparatuses according to the first aspect.

In certain embodiments, the vagal nerve or nerves is a pulmonary branch of the vagal nerve. In certain such embodiments, the apparatus is in signalling contact with the efferent fibres of a pulmonary branch of the vagal nerve.

Implementation of all aspects of the invention (as discussed both above and below) will be further appreciated by reference to FIGS. 2A-2C.

Figure 2A:
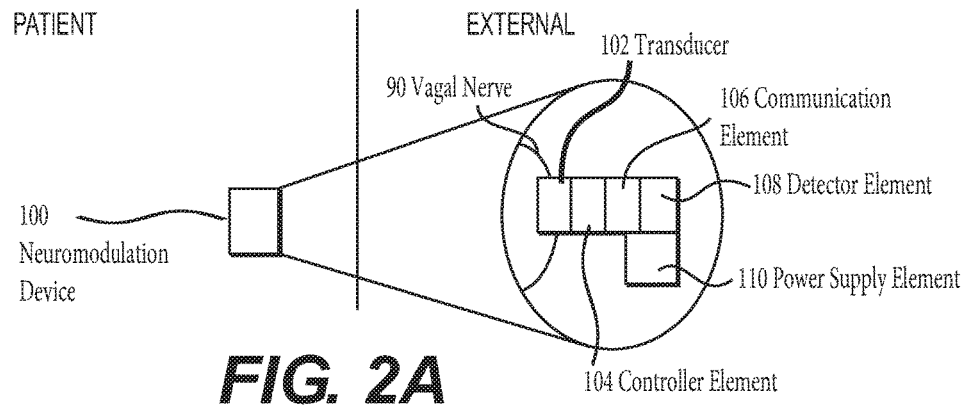
Figure 2B:
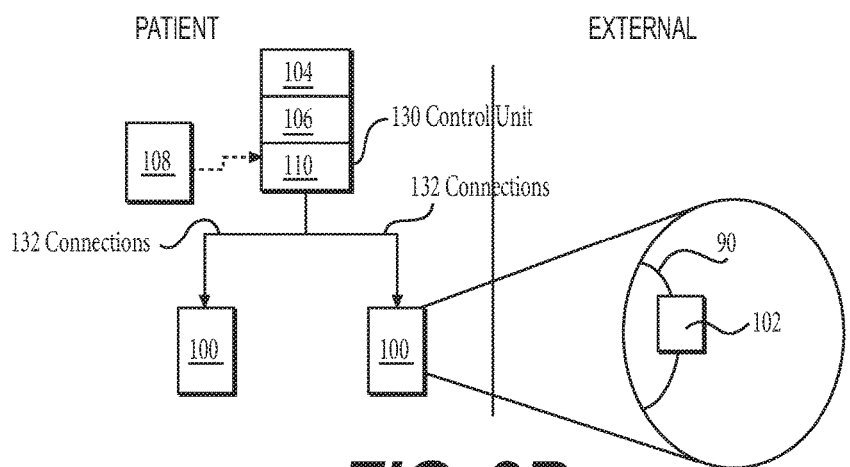
Figure 2C:
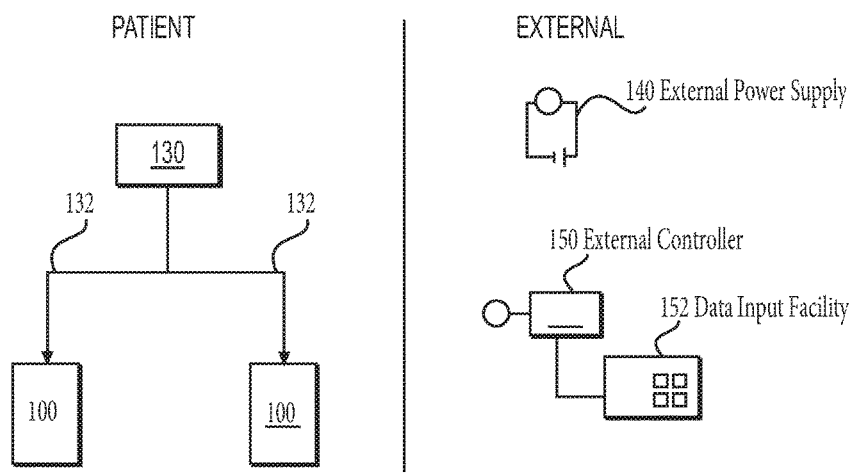

FIGS. 2A-2C show how the invention may be put into effect using one or more neuromodulation devices which are implanted in, located on, or otherwise disposed with respect to a patient in order to carry out any of the various methods described herein. In this way, one or more neuromodulation devices can be used to treat COPD or asthma in a patient, in particular bronchoconstriction associated with COPD or asthma, by modulating neural activity in at least one vagal nerve nerve, for example a pulmonary branch of the vagal nerve, optionally the efferent fibres of a pulmonary branch of the vagal nerve.

In each of the FIGS. 2B-2C a separate neuromodulation device 100 is provided in respect of each of the left and right bronchi, although as discussed herein a device could be provided or used in respect of only one of the left and right bronchi. Each such neuromodulation device may be fully or partially implanted in the patient, or otherwise located, so as to provide neuromodulation of the respective nerve or nerves. Each of the left and right neuromodulation devices 100 may operate independently, or may operate in communication with each other.

FIG. 2A also shows schematically components of an implanted neuromodulation device 100, in which the device comprises several elements, components or functions grouped together in a single unit and implanted in the patient. A first such element is a transducer 102 which is shown in proximity to a vagal nerve 90 of the patient. The transducer 102 may be operated by a controller element 104. The device may comprise one or more further elements such as a communication element 106, a detector element 108, a power supply element 110 and so forth.

Each neuromodulation device 100 may carry out the required neuromodulation independently, or in response to one or more control signals. Such a control signal may be provided by the controller 104 according to an algorithm, in response to output of one or more detector elements 108, and/or in response to communications from one or more external sources received using the communications element. As discussed herein, the detector element(s) could be responsive to a variety of different physiological parameters.

FIG. 2B illustrates some ways in which the apparatus of FIG. 2A may be differently distributed. For example, in FIG. 2B the neuromodulation devices 100 comprise transducers 102 implanted proximally to a vagal nerve 90, but other elements such as a controller 104, a communication element 106 and a power supply 110 are implemented in a separate control unit 130 which may also be implanted in, or carried by the patient. The control unit 130 then controls the transducers in both of the neuromodulation devices via connections 132 which may for example comprise electrical wires and/or optical fibres for delivering signals and/or power to the transducers.

In the arrangement of FIG. 2B one or more detectors 108 are located separately from the control unit, although one or more such detectors could also or instead be located within the control unit 130 and/or in one or both of the neuromodulation devices 100. The detectors may be used to detect one or more physiological parameters of the patient, and the controller element or control unit then causes the transducers to apply the signal in response to the detected parameter(s), for example only when a detected physiological parameter meets or exceeds a predefined threshold value. Physiological parameters which could be detected for such purposes include parasympathetic tone, ASM tone, blood oxygen saturation, blood carbon dioxide concentration, respiratory rate, total lung capacity, and forced expiration volume. Similarly, a detected physiological parameter could be an action potential or pattern of action potentials in a nerve of the patient, for example a vagal nerve, optionally a pulmonary branch of the vagal nerve or efferent fibres thereof, wherein the action potential or pattern of action potentials is associated with bronchospasm.

A variety of other ways in which the various functional elements could be located and grouped into the neuromodulation devices, a control unit 130 and elsewhere are of course possible. For example, one or more sensors of FIG. 2B could be used in the arrangement of FIG. 2A or 2C or other arrangements.

FIG. 2C illustrates some ways in which some functionality of the apparatus of FIG. 2A or 2B is provided not implanted in the patient. For example, in FIG. 2C an external power supply 140 is provided which can provide power to implanted elements of the apparatus in ways familiar to the skilled person, and an external controller 150 provides part or all of the functionality of the controller 104, and/or provides other aspects of control of the apparatus, and/or provides data readout from the apparatus, and/or provides a data input facility 152. The data input facility could be used by a patient or other operator in various ways, for example to input data relating to the respiratory status of the patient (e.g. if they are experiencing bronchospasm, their forced expiration volume).

Each neuromodulation device may be adapted to carry out the neuromodulation required using one or more physical modes of operation which typically involve applying a signal to a vagal nerve, a pulmonary branch of a vagal nerve, or the efferent fibres thereof, such a signal typically involving a transfer of energy to (or from) the nerve(s). As already discussed, such modes may comprise modulating the nerve or nerves using an electrical signal, an optical signal, an ultrasound or other mechanical signal, a thermal signal, a magnetic or electromagnetic signal, or some other use of energy to carry out the required modulation. Such signals may be non-destructive signals. Such modulation may comprise increasing, inhibiting, blocking or otherwise changing the pattern of neural activity in the nerve or nerves. To this end, the transducer 102 illustrated in FIG. 2A could be comprised of one or more electrodes, one or more photon sources, one or more ultrasound transducers, one more sources of heat, or one or more other types of transducer arranged to put the required neuromodulation into effect.

The neural modulation device(s) or apparatus may be arranged to inhibit neural activity of a vagal nerve, a pulmonary branch of a vagal nerve, or the efferent fibres thereof by using the transducer(s) to apply a voltage or current, for example a direct current (DC) such as a charge balanced direct current, or an AC waveform, or both. The device or apparatus may be arranged to use the transducer(s) to apply a DC ramp, then apply a first AC waveform, wherein the amplitude of the waveform increases during the period the waveform is applied, and then apply a second AC waveform.

In certain preferred embodiments, wherein the signal comprises one or more AC waveforms, each AC waveform is independently selected from an AC waveform of 5-25 kHz, optionally 10-25 kHz, optionally 15-25 kHz, optionally 20-25 kHz. In certain preferred embodiments, the signal comprises an AC waveform signal of 5 kHz. In certain alternative preferred embodiments, the signal comprises an AC waveform of 25 kHz.

In certain embodiments, the signal comprises a DC waveform and/or an AC waveform having a voltage of 1-20V. In certain preferred embodiments, the signal has a voltage of 1-15V, 3-15V, 5-15V, optionally 10-15V. In certain preferred embodiments the voltage is selected from 3V, 5V, 10V and 15V.

In certain preferred embodiments, the signal comprises an AC waveform of 5 kHz 3V, or an AC waveform of 5 kHz 15V, or an AC waveform of 25 kHz 5V, or an AC waveform of 25 kHz 5V.

Thermal methods of neuromodulation typically manipulate the temperature of a nerve to inhibit signal propagation.

For example, Patberg et al. (Blocking of impulse conduction in peripheral nerves by local cooling as a routine in animal experimentation; Journal of Neuroscience Methods 1984; 10:267-75, which is incorporated herein by reference) discuss how cooling a nerve blocks signal conduction without an onset response, the block being both reversible and fast acting, with onsets of up to tens of seconds. Heating the nerve can also be used to block conduction, and is generally easier to implement in a small implantable or localised transducer or device, for example using infrared radiation from laser diode or a thermal heat source such as an electrically resistive element, which can be used to provide a fast, reversible, and spatially very localised heating effect (see for example Duke et al. J Neural Eng. 2012 June; 9(3):036003. Spatial and temporal variability in response to hybrid electro-optical stimulation, which is incorporated herein by reference). Either heating, or cooling, or both could be provided using a Peltier element.

Optogenetics is a technique that genetically modifies cells to express photosensitive features, which can then be activated with light to modulate cell function. Many different optogenetic tools have been developed that can be used to inhibit neural firing. A list of optogenetic tools to suppress neural activity has been compiled (Epilepsia. 2014 Oct. 9. doi: 10.1111/epi.12804. WONOEP appraisal: Optogenetic tools to suppress seizures and explore the mechanisms of epileptogenesis. Ritter L M et al., which is incorporated herein by reference). Acrylamine-azobenzene-quaternary ammonium (AAQ) is a photochromic ligand that blocks many types of K+ channels and in the cis configuration, the relief of K+ channel block inhibits firing (Nat Neurosci. 2013 July; 16(7):816-23. doi: 10.1038/nn.3424.

Optogenetic pharmacology for control of native neuronal signaling proteins Kramer R H et al, which is incorporated herein by reference). By adapting Channelrhodopsin-2 and introducing it into mammalian neurons with the lentivirus, it is possible to control inhibitory synaptic transmission (Boyden E S 2005). Instead of using an external light source such as a laser or light emitting diode, light can be generated internally by introducing a gene based on firefly luciferase (Land B B 2014). The internally generated light has been sufficient to generate inhibition.

Mechanical forms of neuromodulation can include the use of ultrasound which may conveniently be implemented using external instead of implanted ultrasound transducers. Other forms of mechanical neuromodulation include the use of pressure (for example see "The effects of compression upon condition in myelinated axons of the isolated frog sciatic nerve" by Robert Fern and P. J. Harrison Br.j. Anaesth. (1975), 47, 1123, which is incorporated herein by reference).

Some electrical forms of neuromodulation may use direct current (DC), or alternating current (AC) waveforms applied to a nerve using one or more electrodes. A DC block may be accomplished by gradually ramping up the DC waveform amplitude (Bhadra and Kilgore, IEEE Transactions on Neural systems and rehabilitation engineering, 2004 12(3) pp 313-324, which is incorporated herein by reference). Some AC techniques include HFAC or KHFAC (high-frequency or kilohertz frequency) to provide a reversible block (for example see Kilgore and Badra, 2004, Medical and Biological Engineering and Computing, the content of which is incorporated herein by reference for all purposes). In the work of Kilgore and Bhadra, a proposed waveform was sinusoidal or rectangular at 3-5 kHz, and typical signal amplitudes that produced block were 3-5 Volts or 0.5 to 2.0 milli Amperes peak to peak.

HFAC may typically be applied at a frequency of between 1 and 50 kHz at a duty cycle of 100% (Bhadra, N. et al., Journal of Computational Neuroscience, 2007, 22(3), pp 313-326, which is incorporated herein by reference). Methods for selectively blocking activity of a nerve by application of a waveform having a frequency of 5-10 kHz are described in U.S. Pat. No. 7,389,145 (incorporated herein by reference). Similarly, U.S. Pat. No. 8,731,676 (incorporated herein by reference) describes a method of ameliorating sensory nerve pain by applying a 5-50 kHz frequency waveform to a nerve.

The techniques discussed above principally relate to the blocking of neuronal activity. Where modulation by increasing activity or otherwise modifying activity in various ways is required, electrodes adjacent to or in contact with the nerve or particular parts of the nerve for example in contact with specific nerve fibres may be used to impart an electrical signal to stimulate activity in various ways, as would be appreciated by the skilled person.

In a third aspect, the invention provides a method of treating COPD or asthma in a patient, in particular bronchoconstriction associated with COPD or asthma, the method comprising applying a signal to a part or all of a vagal nerve of said patient to modulate the neural activity of said nerve in the patient. In certain embodiments, the signal is applied to a pulmonary branch of a vagal nerve. In certain embodiments the signal is applied to the efferent fibres of a pulmonary branch of a vagal nerve.

In certain embodiments, the signal is applied by a neuromodulation device comprising one or more transducers configured to apply the signal. In certain preferred embodiments the neuromodulation device is at least partially implanted in the patient. In certain preferred embodiments, the neuromodulation device is wholly implanted in the patient.

In certain embodiments, the treatment of COPD or asthma, in particular COPD-associated or asthma-associated bronchoconstriction, is prophylactic treatment. That is, the methods of the invention reduce the frequency of bronchoconstriction episodes. In certain preferred such embodiments, the method prevents the onset of bronchoconstriction.

In certain embodiments, the treatment of COPD or asthma, in particular COPD-associated or asthma-associated bronchoconstriction, is therapeutic treatment. That is, the methods of the invention at least partially relieve or ameliorate the severity of a bronchoconstriction episode. In certain such embodiments, the methods of the invention wholly relieve a bronchoconstriction episode—that is, the episode is stopped by use of the method and the patient is able to breath normally.

In certain embodiments, treatment of COPD or asthma, in particular COPD-associated or asthma-associated bronchoconstriction, is indicated by an improvement in a measurable physiological parameter, for example a reduction in parasympathetic tone, a decrease in airway smooth muscle tone, an increase in blood oxygen saturation, a decrease in blood carbon dioxide concentration, a decrease in respiratory rate, an increase in total lung capacity, an increase in forced expiration volume.

Suitable methods for determining the value for any given parameter would be appreciated by the skilled person.

In certain embodiments, treatment of the condition is indicated by an improvement in the profile of neural activity in the nerve or nerves to which the signal is applied. That is, treatment of the condition is indicated by the neural activity in the nerve(s) approaching the neural activity in a healthy individual—i.e. the pattern of action potentials in the nerve more closely resembling that exhibited by a healthy individual than before the intervention.

In certain embodiments the modulation in neural activity as a result of applying the signal is inhibition of neural activity in the nerve or nerves to which a signal is applied. That is, in such embodiments, application of the signal results in the neural activity in at least part of the nerve(s) being reduced compared to the neural activity in that part of the nerve(s) prior to the signal being applied. Therefore, in certain embodiments, a result of applying the signal is at least partial inhibition of neural activity in the nerve or nerves. In certain embodiments, a result of applying the signal is full inhibition of neural activity in the nerve or nerves.

In certain embodiments, the inhibition in neural activity as a result of applying the signal is a block on neural activity in the nerve(s) to which a signal is applied. That is, in such embodiments, the application of the signal blocks action potentials from travelling beyond the point of the block in the part of the nerve(s) to which the signal is applied. In certain such embodiments, the modulation is a partial block—that is, neural activity is blocked in part of the nerve to which the signal is applied, for example a subset of nerve fibres. In certain alternative embodiments, the modulation is a full block—that is, neural activity is blocked in all of the nerve to which the signal is applied.

In certain embodiments the signal applied to the nerve is a signal that inhibits (e.g. blocks) neural activity and limits or prevents onset effect.

An example of such a signal that limits or prevents onset effect is a signal that comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform.

In certain embodiments, the modulation in neural activity as a result of applying the signal is an increase in neural activity in the nerve or nerves. That is, in such embodiments, application of the signal results in the neural activity in at least part of the nerve(s) being increased compared to the baseline neural activity in that part of the nerve.

In certain embodiments, the modulation in neural activity as a result of applying the signal is an alteration to the pattern of action potentials in nerve or nerves to which a signal is applied. In certain such embodiments, the neural activity is modulated such that the resultant pattern of action potentials in the nerve or nerves resembles the pattern of action potentials in the nerve(s) observed in a healthy subject.

In certain embodiments, the signal is applied intermittently. In certain such embodiments, the signal is applied for a first time period, then stopped for a second time period, then reapplied for a third time period, then stopped for a fourth time period. In such an embodiment, the first, second, third and fourth periods run sequentially and consecutively. The series of first, second, third and fourth periods amounts to one application cycle. In certain such embodiments, multiple application cycles can run consecutively such that the signal is applied in phases, between which phases no signal is applied.

In such embodiments, the duration of the first, second, third and fourth time periods is independently selected. That is, the duration of each time period may be the same or different to any of the other time periods. In certain such embodiments, the duration of each of the first, second, third and fourth time periods is any time from 5 seconds (5 s) to 24 hours (24 h), 30 s to 12 h, 1 min to 12 h, 5 min to 8 h, 5 min to 6 h, 10 min to 6 h, 10 min to 4 h, 30 min to 4 h, 1 h to 4 h. In certain embodiments, the duration of each of the first, second, third and fourth time periods is 5 s, 10 s, 30 s, 60 s, 2 min, 5 min, 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h, 24 h.

In certain embodiments wherein the signal is applied intermittently, the signal is applied for a specific amount of time per day. In certain such embodiments, the signal is applied for 10 min, 20 min, 30 min, 40 min, 50 min, 60 min, 90 min, 2 h, 3 h, 4 h, 5 h, 6 h, 7 h, 8 h, 9 h, 10 h, 11 h, 12 h, 13 h, 14 h, 15 h, 16 h, 17 h, 18 h, 19 h, 20 h, 21 h, 22 h, 23 h per day. In certain such embodiments, the signal is applied continuously for the specified amount of time. In certain alternative such embodiments, the signal may be applied discontinuously across the day, provided the total time of application amounts to the specified time.

In certain embodiments wherein the signal is applied intermittently, the signal is applied only when the patient is in a specific state. In certain such embodiments, the signal is applied only when the patient is in a state of bronchospasm. In such embodiments, the status of the patient (e.g. that they are experiencing bronchospasm) can be indicated by the patient. In alternative such embodiments, the status of the patient can be detected independently from any input from the patient. In certain embodiments in which the signal is applied by a neuromodulation device, the device further comprises a detector configured to detect the status of the patient, wherein the signal is applied only when the detector detects that the patient is in the specific state.

In certain embodiments of methods according to the invention, the method further comprises the step of detecting one or more physiological parameters of the patient, wherein the signal is applied only when the detected physiological parameter meets or exceeds a predefined threshold value. In such embodiments wherein more than one physiological parameter is detected, the signal may be applied when any one of the detected parameters meets or exceeds its threshold value, alternatively only when all of the detected parameters meet or exceed their threshold values. In certain embodiments wherein the signal is applied by a neuromodulation device, the device further comprises at least one detector element configured to detect the one or more physiological parameters.

In certain embodiments, the one or more detected physiological parameters are selected from: parasympathetic tone, ASM tone, blood oxygen saturation, blood carbon dioxide concentration, respiratory rate, total lung capacity, and forced expiration volume.

Similarly, in certain embodiments the detected physiological parameter could be an action potential or pattern of action potentials in a nerve of the patient, for example a vagal nerve, optionally a pulmonary branch of the vagal nerve or efferent fibres thereof, wherein the action potential or pattern of action potentials is associated with bronchospasm.

It will be appreciated that any two or more of the indicated physiological parameters may be detected in parallel or consecutively. For example, in certain embodiments, the pattern of action potentials in the efferent fibres of a pulmonary branch of the vagal nerve can be detected at the same time as blood oxygen saturation.

In certain embodiments, the signal is permanently applied. That is, once begun, the signal is continuously applied to the nerve or nerves. It will be appreciated that in embodiments wherein the signal is a series of pulses, gaps between pulses do not mean the signal is not continuously applied.

In certain embodiments of the methods, the modulation in neural activity caused by the application of the signal (whether that is an increase, inhibition, block or other modulation of neural activity) is temporary. That is, upon cessation of the signal, neural activity in the nerve or nerves returns substantially towards baseline neural activity within 1-60 seconds, or within 1-60 minutes, or within 1-24 hours, optionally 1-12 hours, optionally 1-6 hours, optionally 1-4 hours, optionally 1-2 hours. In certain such embodiments, the neural activity returns substantially fully to baseline neural activity. That is, the neural activity following cessation of the signal is substantially the same as the neural activity prior to the signal being applied—i.e. prior to modulation.

In certain alternative embodiments, the modulation in neural activity caused by the application of the signal is substantially persistent. That is, upon cessation of the signal, neural activity in the nerve or nerves remains substantially the same as when the signal was being applied—i.e. the neural activity during and following modulation is substantially the same.

In certain embodiments, the modulation in neural activity caused by the application of the signal is partially corrective, preferably substantially corrective. That is, upon cessation of the signal, neural activity in the nerve or nerves more closely resembles the pattern of action potentials observed in a healthy subject than prior to modulation, preferably substantially fully resembles the pattern of action potentials observed in a healthy subject. In such embodiments, the modulation caused by the signal can be any modulation as defined herein. For example, application of the signal may result in a block on neural activity, and upon cessation of the signal, the pattern of action potentials in the nerve or nerves resembles the pattern of action potentials observed in a healthy subject. By way of further example, application of the signal may result in modulation such that the neural activity resembles the pattern of action potentials observed in a healthy subject, and upon cessation of the signal, the pattern of action potentials in the nerve resembles the pattern of action potentials observed in a healthy subject. It is hypothesised that such a corrective effect is the result of a positive feedback loop.

In certain such embodiments, once first applied, the signal may be applied intermittently or permanently, as described in the embodiments above.

In certain embodiments, the signal is applied to one or more pulmonary branches of a vagal nerve of said patient, preferably the efferent nerve fibres of said nerve or nerves, to modulate the neural activity said nerve or nerves in the patient.

As is known by the skilled person, mammals have a left and a right bronchial tree, each being innervated by pulmonary branches of the vagal nerve (FIG. 1). Therefore, in certain embodiments, the signal is applied bilaterally. That is, in such embodiments, the signal is applied to a pulmonary branch of a vagal nerve on both the left and right side of the patient such that the neural activity is modulated in the nerves to which the signal is applied—i.e. the modulation is bilateral. In such embodiments, the signal applied to each nerve, and therefore the type and extent of modulation is independently selected from that applied to the other nerve or nerves. In certain embodiments the signal applied to the right nerve or nerves is the same as the signal applied to the left nerve or nerves. In certain alternative embodiments the signal applied to the right nerve or nerves is different to the signal applied to the left nerve or nerves.

In certain embodiments wherein the modulation is bilateral, each signal is applied by a neuromodulation device comprising one or more transducers for applying the signal. In certain such embodiments, all signals are applied by the same neuromodulation device, that device have at least two transducers, one to apply the signal to the left nerve(s) and one to apply the signal to the right nerve(s). In certain alternative embodiments, the each signal is applied by a separate neuromodulation device.

In certain embodiments, the signal applied is a non-destructive signal.

In certain embodiments of the methods according to the invention, the signal applied is an electrical signal, an electromagnetic signal (optionally an optical signal), a mechanical (optionally ultrasonic) signal, a thermal signal, a magnetic signal or any other type of signal.

In certain such embodiments in which more than one signal may be applied, for example when the modulation is bilateral, each signal may be independently selected from an electrical signal, an optical signal, an ultrasonic signal, and a thermal signal. In those such embodiments in which two signals are applied by one modulation device, the two signals may be the same type of signal or may be different types of signal independently selected from an electrical signal, an optical signal, an ultrasonic signal, and a thermal signal. In those embodiments in which two signals are applied, each by a separate neuromodulation device, the two signals may be the same type of signal or may be different types of signal independently selected from an electrical signal, an optical signal, an ultrasonic signal, and a thermal signal.

In certain embodiments in which the signal is applied by a neuromodulation device comprising at least one transducer, the transducer may be comprised of one or more electrodes, one or more photon sources, one or more ultrasound transducers, one more sources of heat, or one or more other types of transducer arranged to put the signal into effect.

In certain embodiments, the signal is an electrical signal, for example a voltage or current. In certain such embodiments the signal comprises a direct current (DC) waveform, such as a charge balanced DC waveform, or an alternating current (AC) waveform, or both a DC and an AC waveform.

In certain embodiments the signal comprises a DC ramp followed by a plateau and charge-balancing, followed by a first AC waveform, wherein the amplitude of the first AC waveform increases during the period in which the first AC waveform is applied, followed by a second AC waveform having a lower amplitude and/or lower frequency than the first AC waveform. In certain such embodiments, the DC ramp, first AC waveform and second AC waveform are applied substantially sequentially. Such a signal will be advantageous in limiting or preventing onset effect that may be associated with a kilohertz frequency AC waveform used to inhibit (e.g. block) neural activity.

In certain preferred embodiments, wherein the signal comprises one or more AC waveforms, each AC waveform is independently selected from an AC waveform of 5-25 kHz, optionally 10-25 kHz, optionally 15-25 kHz, optionally 20-25 kHz. In certain preferred embodiments, the signal comprises an AC waveform signal of 5 kHz. In certain alternative preferred embodiments, the signal comprises an AC waveform of 25 kHz.

In certain embodiments, the signal comprises a DC waveform and/or an AC waveform having a voltage of 1-20V. In certain preferred embodiments, the signal has a voltage of 1-15V, 3-15V, 5-15V, optionally 10-15V. In certain preferred embodiments the voltage is selected from 3V, 5V, 5V and 15V.

In certain preferred embodiments, the signal comprises an AC waveform of 5 kHz 3V, or an AC waveform of 5 kHz 15V, or an AC waveform of 25 kHz 5V, or an AC waveform of 25 kHz 5V.

In certain embodiments wherein the signal is a thermal signal, the signal reduces the temperature of the nerve (i.e. cools the nerve). In certain alternative embodiments, the signal increases the temperature of the nerve (i.e. heats the nerve). In certain embodiments, the signal both heats and cools the nerve.

In certain embodiments wherein the signal is a mechanical signal, the signal is an ultrasonic signal. In certain alternative embodiments, the mechanical signal is a pressure signal.

In a fourth aspect, the invention provides a neuromodulatory electrical waveform for use in treating COPD or asthma, in particular COPD-associated or asthma-associated bronchoconstriction, in a patient, wherein the waveform is a kiloHertz alternating current (AC) waveform having a frequency of 5-25 kHz, such that, when applied to a vagal nerve, preferably a pulmonary branch of the vagal nerve, of the patient, the waveform inhibits neural signalling in the nerve. In certain embodiments, the waveform, when applied to the nerve, relieves or prevents bronchoconstriction.

In a fifth aspect, the invention provides use of a neuromodulation device for treating COPD or asthma, in particular COPD-associated or asthma-associated bronchoconstriction in a patient by modulating neural activity in a vagal nerve of the patient, preferably a pulmonary branch of the vagal nerve, more preferably the efferent fibres of said pulmonary branch of the vagal nerve.

In a preferred embodiment of all aspects of the invention, the subject or patient is a mammal, more preferably a human.

In a preferred embodiment of all aspects of the invention, the signal or signals is/are applied substantially exclusively to the nerves or nerve fibres specified, and not to other nerves or nerve fibres.

The foregoing detailed description has been provided by way of explanation and illustration, and is not intended to limit the scope of the appended claims. Many variations in the presently preferred embodiments illustrated herein will be apparent to one of ordinary skill in the art, and remain within the scope of the appended claims and their equivalents.

EXAMPLES

Example 1

Ex Vivo Model of Bronchoconstriction

The methods for studying vagally-mediated bronchoconstriction have been described in detail elsewhere (Canning et al., Am J Physiol Regul Integr Comp Physiol. 2002 August; 283(2):R320-30). The airways and associated nerves are dissected free of all extraneous tissues and placed in water-jacketed dissecting dish continuously perfused with warmed, oxygenated Krebs buffer. A mainstem bronchus is isolated with associated nerves intact. Stirrups are placed on either side of the bronchus, with one fixed to the bottom of the recording chamber and the second attached to an isometric force transducer. The associated vagus nerves are stimulated (0.1-64 Hz) electrically using bipolar electrodes, resulting in muscle contraction.

In an isolated ex vivo guinea pig vagus-bronchus preparation, a low frequency electrical stimulation of the whole vagus nerve activates preganglionic_parasympathetic nerves lead to a rapid cholinergic contraction of the bronchus. An optimum signal for evoking bronchoconstriction in the ex vivo guinea pig model is 16 Hz, 10V for 10 s every 2 minutes. Such a stimulus induces a compound action potential in the vagus nerve (FIG. 3A), that leads to contraction of the ASM.

Figure 3B:
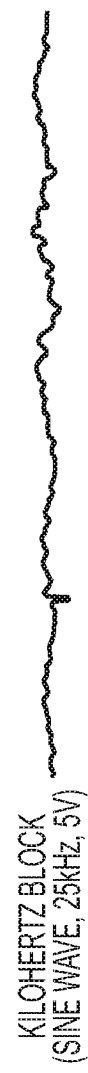
Figure 3C:
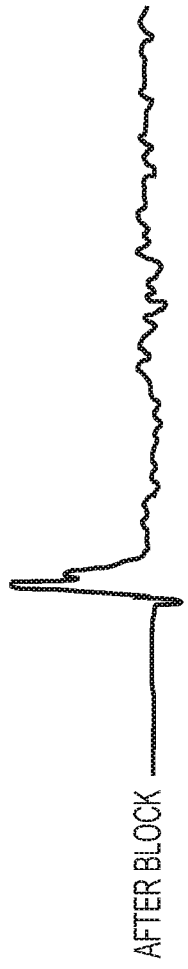

Application of an electrical signal (25 kHz, 5V) to the vagus nerve is able to block the induced action potential (FIG. 3B). This high frequency kilohertz block on the action potential is temporary, as once the signal is no longer applied, the action potential is still able to be induced when the low frequency stimulating signal is applied (FIG. 3C).

Figure 4A:
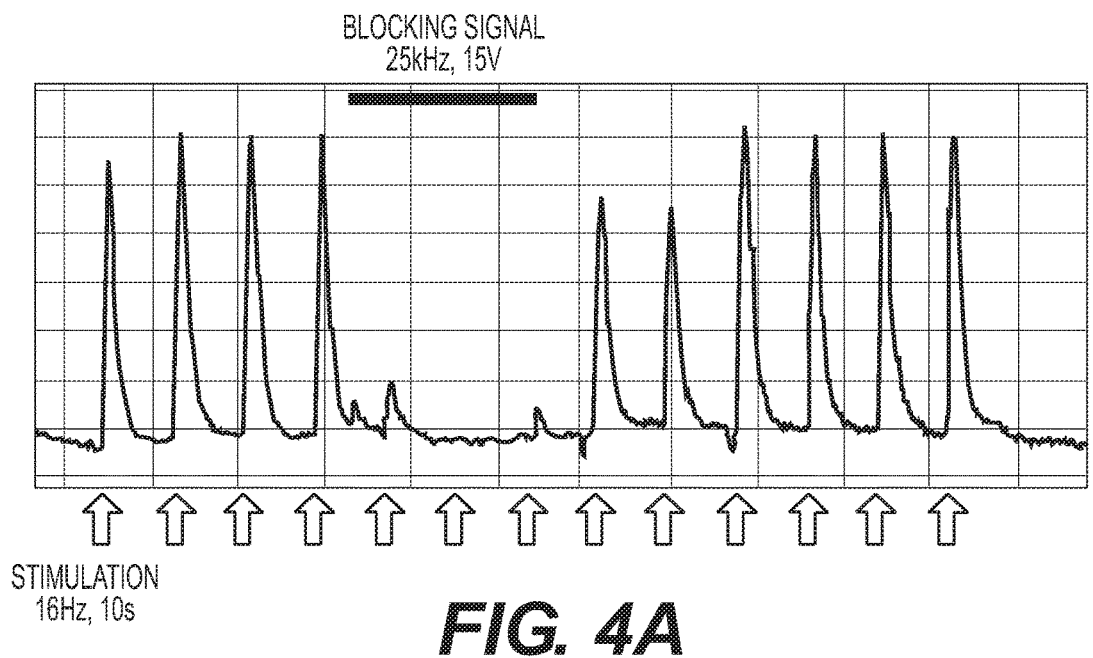
Figure 4B:
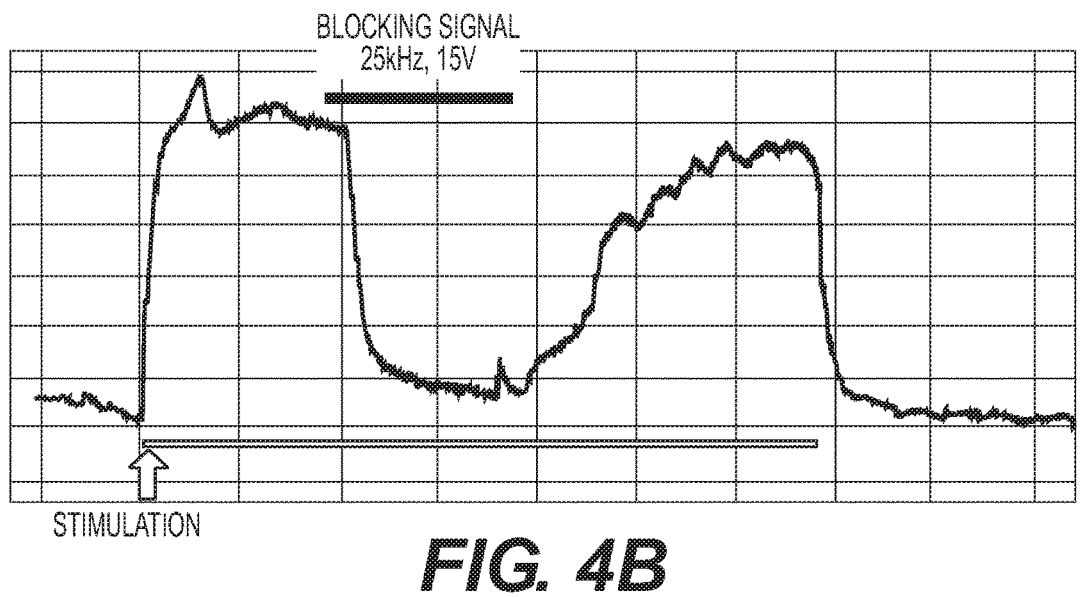

The efficacy of the kilohertz electrical block in preventing and reversing airway smooth muscle (ASM) contractions was demonstrated in an in vitro model (FIG. 4). When a neuromodulatory blocking signal of 25 kHz 15V was applied prior to and during the contraction-inducing stimulus (16 Hz, 10 s), ASM contraction was prevented (FIG. 4A). Similarly, when the same kilohertz block (25 kHz, 15V) was applied during a period of sustained induced ASM contractions, the level of contraction returned to normal, non-induced levels (FIG. 4B).

Example 2

Ex-Vivo Assessment of KFAC on Compound Action Potential Conduction in Whole Vagus Nerve and Thoracic Branches Vagus nerves obtained from guinea pigs and vagus thoracic branches obtained from human organ donors were dissected free from surrounding tissues. One end of the cut vagus nerve or branch was stimulated via suction electrodes attached to a stimulator that delivered single rectangular pulses. Compound action potentials were recorded at the other end of vagus nerve or thoracic branch nerve using a conventional recording suction electrode. The resulting signals were amplified (AM Systems, Model 1800), displayed on an oscilloscope and stored on a computer. During application of a neuromodulatory electrical signal between the stimulating and recording electrode, the amplitude of the waves in the compound action potential are reduced compared with the amplitude recorded prior to the application of the neuromodulatory signal (FIG. 8, Direct Current) and FIG. 9, Alternating Current). This inhibitory effect is absent when the application of the neuromodulation signal is stopped (FIGS. 8 and 9). This indicates that the application of the signal did not irreversibly damage the nerve.

Example 3

In Vivo Model of Bronchoconstriction

Methods for studying vagally-mediated bronchospasm in anesthetized guinea pigs have been described in detail elsewhere (Mazzone and Canning, Curr Protoc Pharmacol. 2002 May 1; Chapter 5:Unit 5.26; Auton Neurosci. 2002 Aug. 30; 99(2):91-101) and shown in FIG. 10. Guinea pigs are anesthetized with urethane (1.5 g/kg ip). The trachea and vagus nerves are visualized by a midline incision in the neck. The trachea is cannulated and connected to a constant volume ventilator (6 mL/kg body weight). The animals are then paralyzed with succinylcholine (2.5 mg/kg sc). An artery and vein are cannulated to monitor cardiovascular parameters and for drug delivery. The vagus nerves are placed on bipolar electrodes. A pressure transducer connected to a sideport of the tracheal cannula is used to monitor pulmonary inflation pressure. Bronchospasm is recorded as a percentage increase in pulmonary inflation pressure.

An in vivo guinea pig model of bronchoconstriction was also developed. A pulmonary branch of a vagal nerve of anaesthetised, paralysed and mechanically ventilated guinea pigs was exposed and an electrode applied. A stimulatory signal of 16 Hz, 10V for 10 s was applied to the exposed vagal nerve to induced bronchoconstriction. Bronchoconstriction was indicated by an increase in the pulmonary inflation pressure (PIP), indicative of increased parasympathetic neural activity (FIGS. 5 A and B). A stimulation of 25 Hz for 7 s is also able to induce bronchoconstriction (Hoffmann et al. Neuromodulation 2012; 15: 527-536, which is incorporated herein by reference in its entirety).

The ability of a low frequency (16 Hz) stimulatory signal to induce an increase in PIP indicative of bronchoconstriction is also shown in FIG. 6 (Control). When a neuromodulatory electrical signal (a kilohertz block of 5 kHz, 15V) is applied to a pulmonary branch of a vagus nerve, the bronchoconstriction-induced increase in PIP is prevented (FIG. 6—Block). This effect is temporary, as once the neuromodulatory block is no longer applied, the animal exhibits a substantially normal constriction response to the low frequency stimulus (FIG. 6—Recovery). This indicates that the application of the signal did not adversely affect the ability of nerve to propagate action potentials.

High frequency electrical block of vagal nerve activity is also able to be achieved with implanted electrodes. Tunnel or sling cuff electrodes (for example those produced by MicroProbes™ and CorTec™) positioned on one or more pulmonary branches of the right vagus nerve were able to block induced action potentials by applying a kilohertz electrical block signal (5 kHz, 3V) (FIG. 7).

Example 4

In-Vivo Model of Baseline Airway Smooth Muscle Tone

Using the method illustrated in FIG. 10, the portion of the trachea where isometric tension was measured (rings 6 and 7 caudal to the larynx) was perfused with warmed (37° C.), oxygenated Krebs buffer, which was used for selective delivery of atropine (1 M) to the trachea. On-going tonic activity in parasympathetic vagal nerves results in baseline tone in airway smooth muscle. When atropine or a neuromodulatory electrical signal (alternating current 20 kHz, 7 mA) is applied to both right and left vagus nerves a decrease in baseline airway smooth muscle tone is seen (FIG. 11). This effect is maintained until the application of the signal is stopped, at which time baseline tone increases toward its pre-treatment level (FIG. 11) The magnitude of this inhibition was 77+/−8% of the inhibition resulting from application of the atropine (FIGS. 11 and 12). However, the onset of the inhibition of baseline airway smooth tone occurred faster than that seen following treatment with atropine (FIG. 11). The neuromodulatory signal had minimal effect on heart rate or blood pressure (FIG. 12).

The invention claimed is:

1. An apparatus for inhibiting the neural activity of a vagal nerve of a patient, the apparatus comprising:
   one or more transducers each configured to apply a signal to a vagal nerve of the patient; and
   a controller coupled to the one or more transducers, the controller controlling the signal to be applied by each of the one or more transducers, so that the signal inhibits the neural activity of the vagal nerve to reduce parasympathetic tone response in the patient;
   wherein, upon cessation of the signal application, the modulation in neural activity remains substantially the same as when the signal was being applied by the one or more transducers, and wherein the modulation in neural activity as a result of the one or more transducers applying the signal is substantially persistent.

* * * * *